United States Patent [19]

Mikhail

[11] Patent Number: 5,308,350
[45] Date of Patent: May 3, 1994

[54] FEMORAL DISTRACTOR FOR USE IN KNEE SURGERY

[76] Inventor: W. E. Michael Mikhail, 4203 Shamley Green, Toledo, Ohio 43623

[21] Appl. No.: 990,435

[22] Filed: Dec. 15, 1992

Related U.S. Application Data

[60] Continuation-in-part of Ser. No. 871,036, Apr. 20, 1992, which is a division of Ser. No. 508,090, Apr. 11, 1990, Pat. No. 5,217,463.

[51] Int. Cl.⁵ ............................................. A61B 17/56
[52] U.S. Cl. ........................................ 606/88; 606/53; 606/86; 606/90
[58] Field of Search ....................... 606/53, 60, 86–90, 606/105; 128/20

[56] References Cited

U.S. PATENT DOCUMENTS

| | | |
|---|---|---|
| 2,695,607 | 11/1954 | Hipps et al. |
| 3,731,673 | 5/1973 | Halloran |
| 3,750,652 | 8/1973 | Sherwin |
| 3,776,240 | 12/1973 | Woodson |
| 3,801,989 | 4/1974 | McKee |
| 3,955,568 | 5/1976 | Neufeld |
| 4,190,042 | 2/1980 | Sinnreich |
| 4,355,631 | 10/1982 | LeVahn |
| 4,481,947 | 11/1984 | Chester |
| 4,501,266 | 2/1985 | McDaniel |
| 4,520,797 | 6/1985 | Peterson |
| 4,567,885 | 2/1986 | Ardrophy ........................ 606/88 |
| 4,686,972 | 8/1987 | Kurland |
| 4,726,356 | 2/1988 | Santilli et al. |
| 4,738,248 | 4/1988 | Ray |
| 4,747,395 | 5/1988 | Brief |
| 5,002,547 | 3/1991 | Poggie et al. ................... 606/88 |
| 5,171,245 | 12/1992 | Lezana ............................. 606/86 |

FOREIGN PATENT DOCUMENTS

| | | |
|---|---|---|
| 215468 | 11/1984 | Fed. Rep. of Germany |
| 462077 | 9/1913 | France |
| 1487486 | 7/1967 | France |
| 634740 | 11/1978 | U.S.S.R. |
| 1445718 | 12/1988 | U.S.S.R. |
| 1274432 | 5/1972 | United Kingdom |

OTHER PUBLICATIONS

Stille (1939) Catalog of Stainless Steel Retractors.
D. H. Levinthal, Journal of bone & Joint Surgery (1931) "Knee Joint Retractors For Resections and Arthroplasties" pp. 378, 379.
Zimmer Inc. Catalog (1966), pp. 116, 117 and A163.
Brochure of Innomed, Inc., Mentone, Ind., copyrighted 1989 entitled "Mark II Chandler Retractor".
Brochure for "Eftekhar II Knee Prosthesis", undated.
Brochure for DePuy "New Jersey Tri-Compartmental Total Knee System", 1984, DePuy, Inc.

Primary Examiner—C. Fred Rosenbaum
Assistant Examiner—Corrine Maglione
Attorney, Agent, or Firm—Emch, Schaffer, Schaub & Porcello Co.

[57] ABSTRACT

A femoral distractor for use in performing knee surgery includes a rod for insertion in the medullary canal of a human femur and a detachable handle assembly. The detachable handle assembly permits the leg of the patient to be moved between positions of extension and flexion without the necessity of removing the rod from the medullary canal by simply removing the handle assembly from such rod.

8 Claims, 15 Drawing Sheets

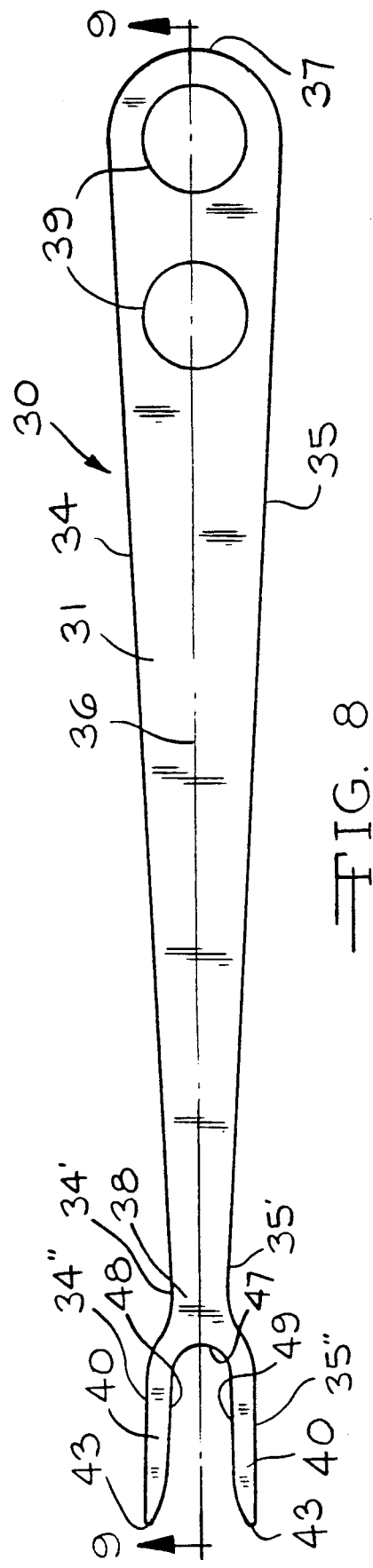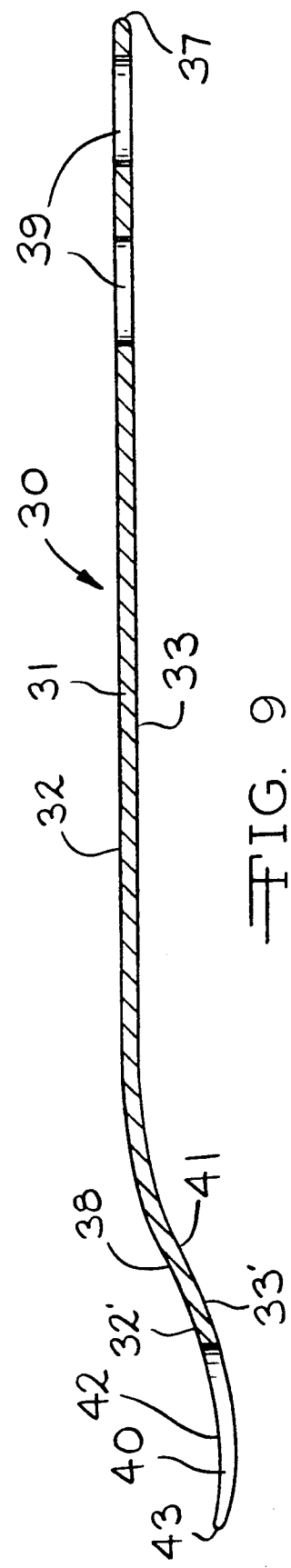

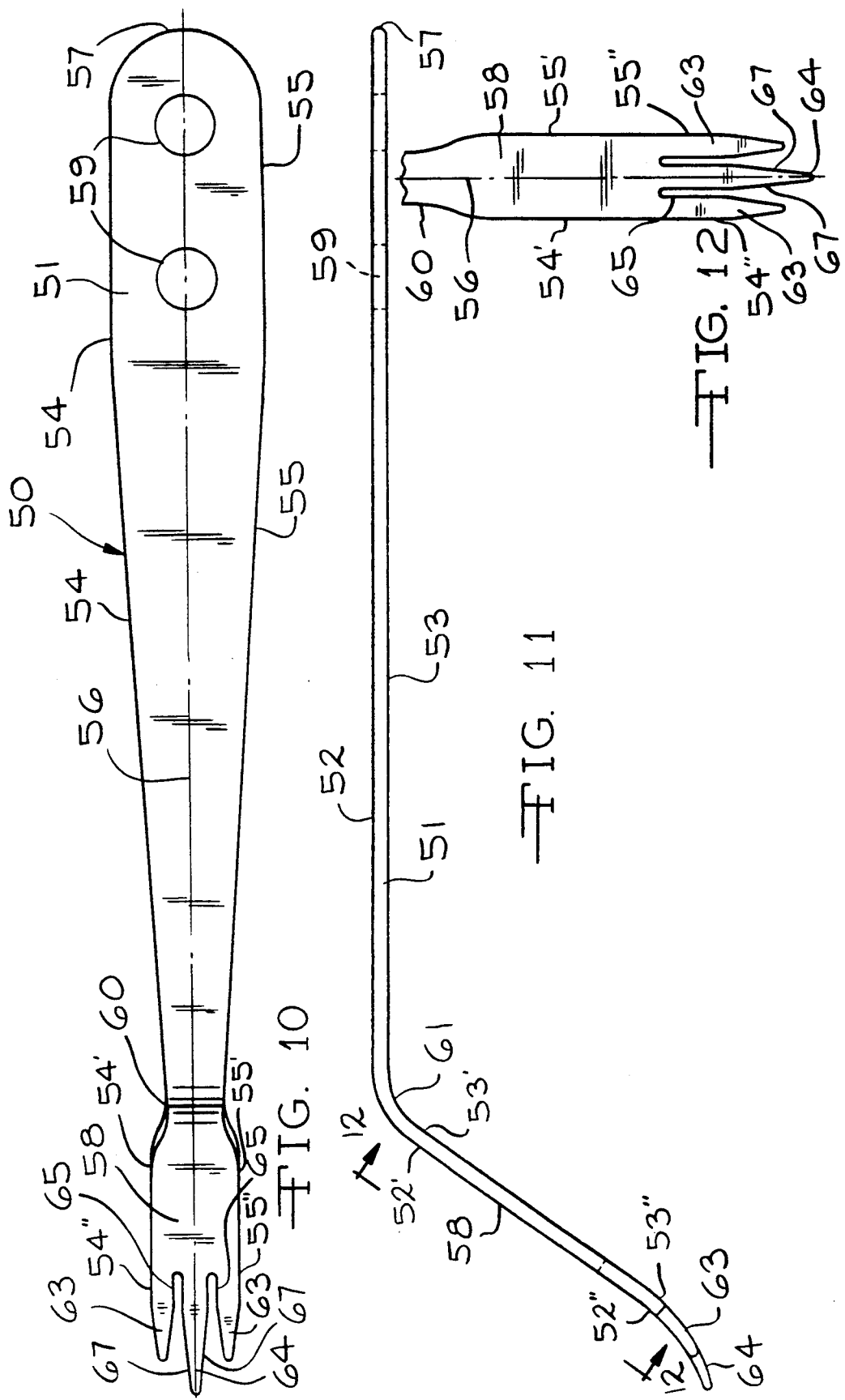

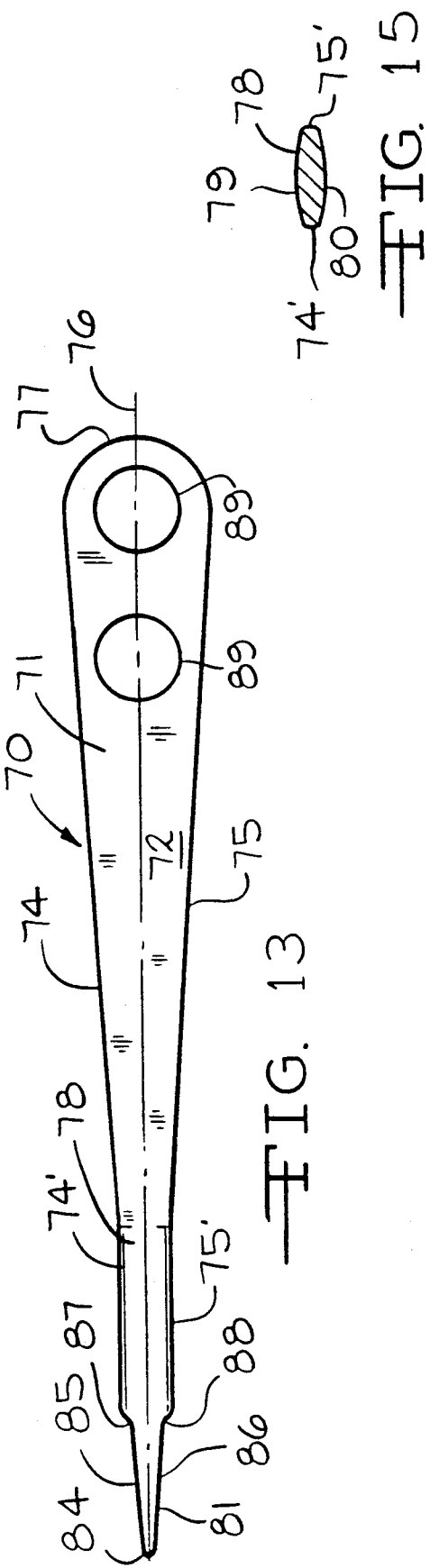
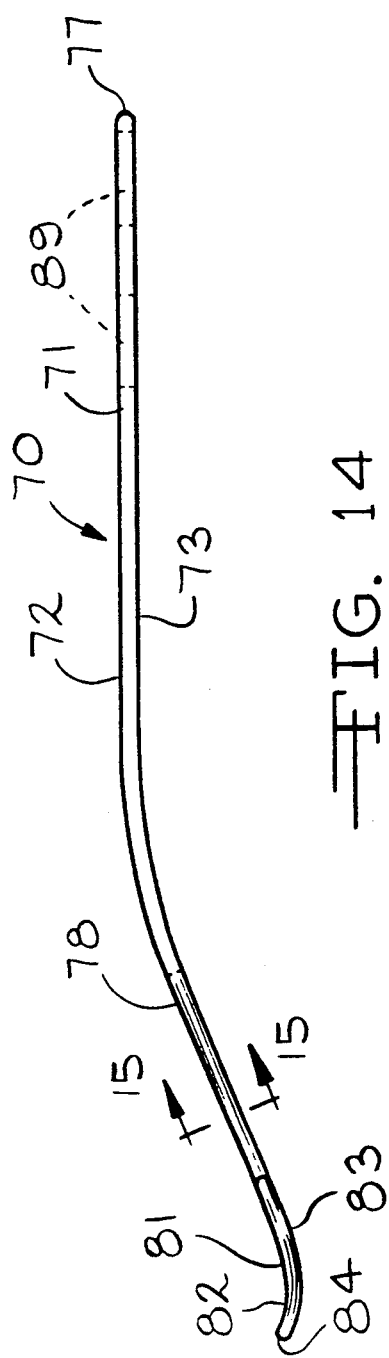
FIG. 15
FIG. 13
FIG. 14

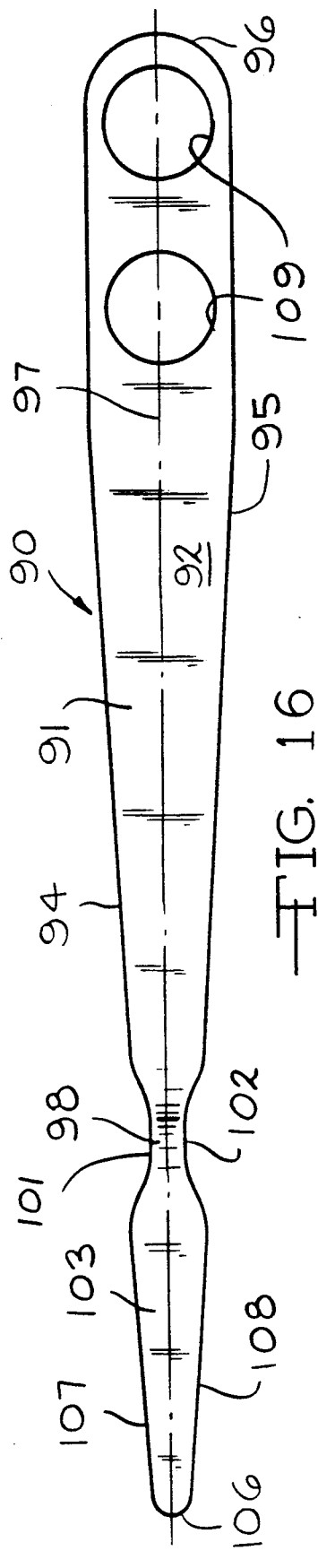
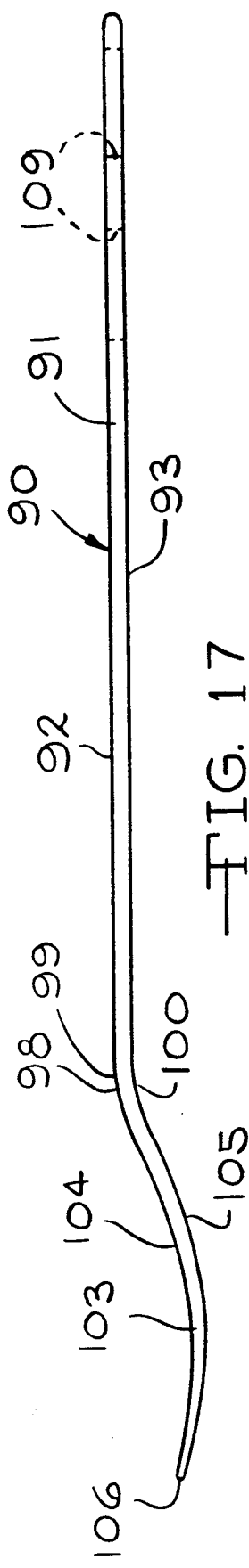
FIG. 16
FIG. 17

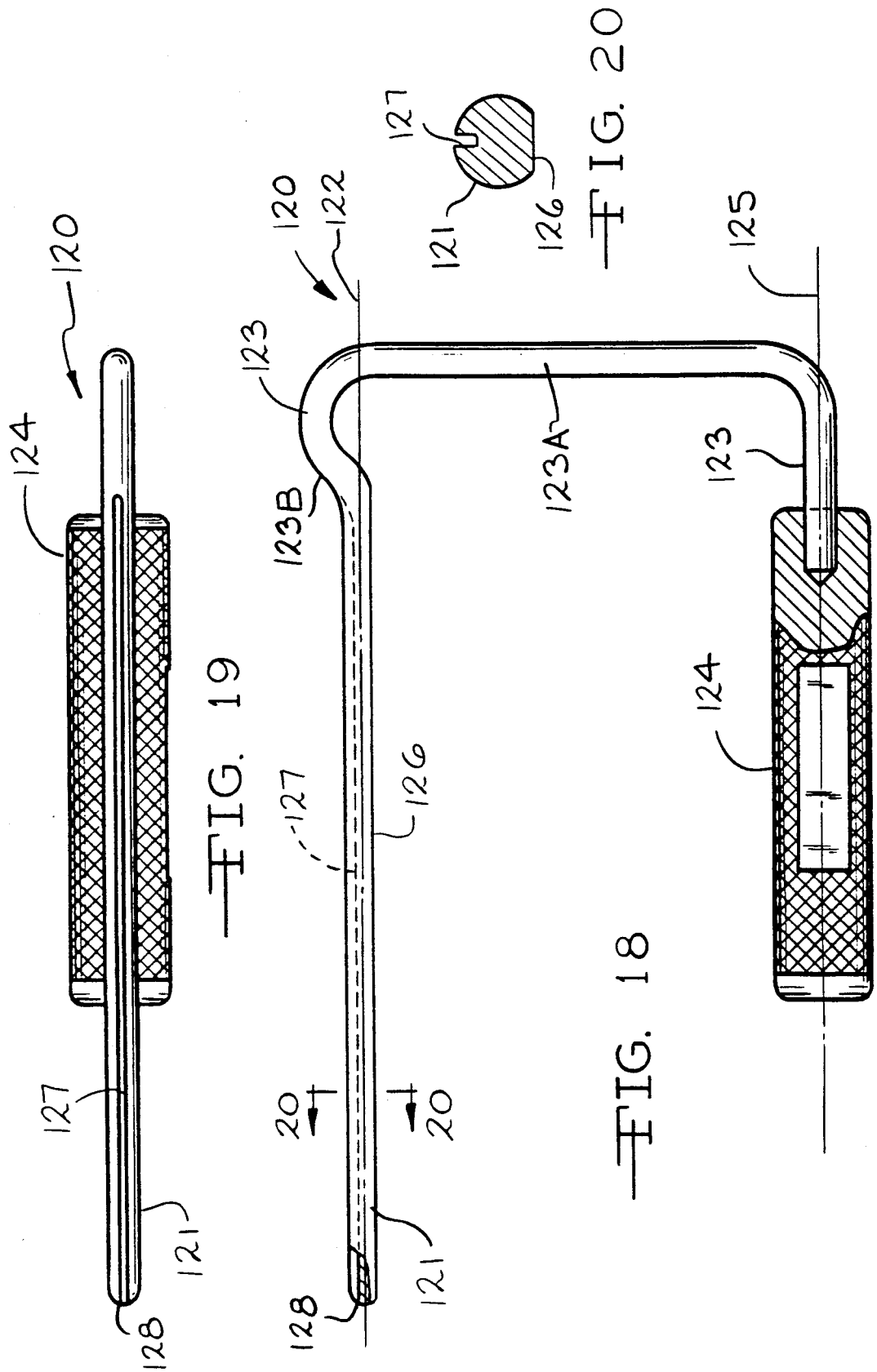

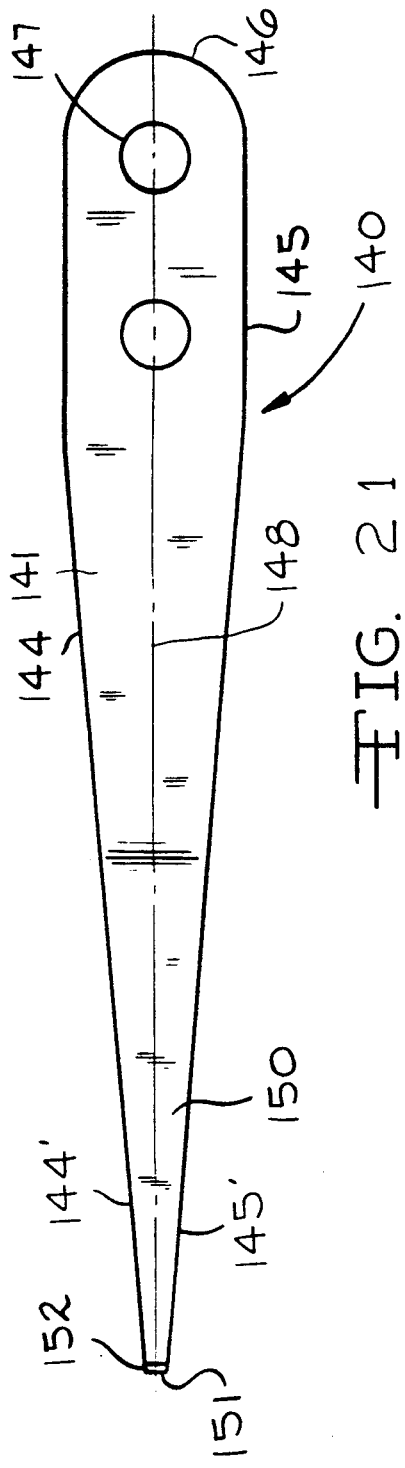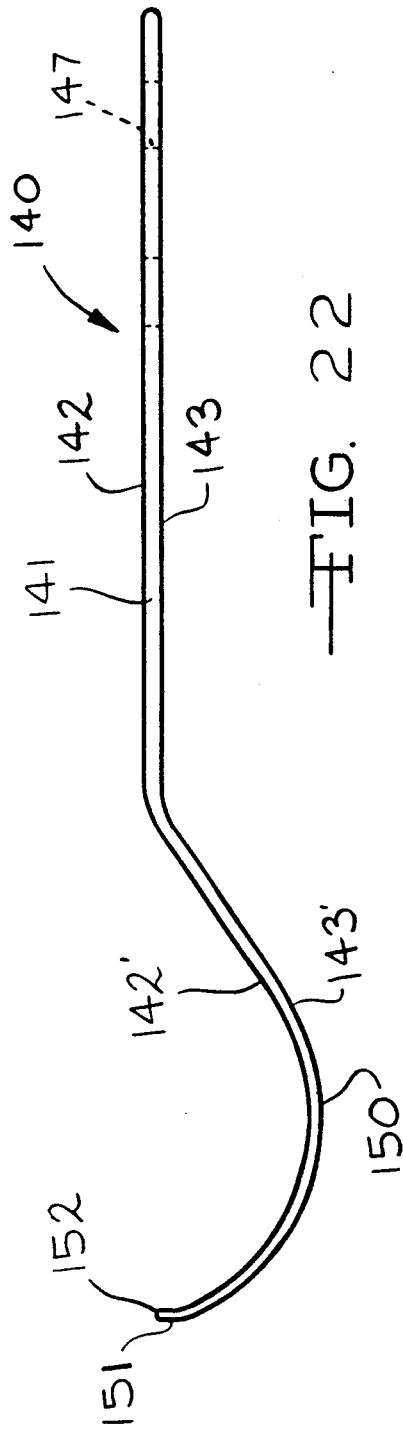

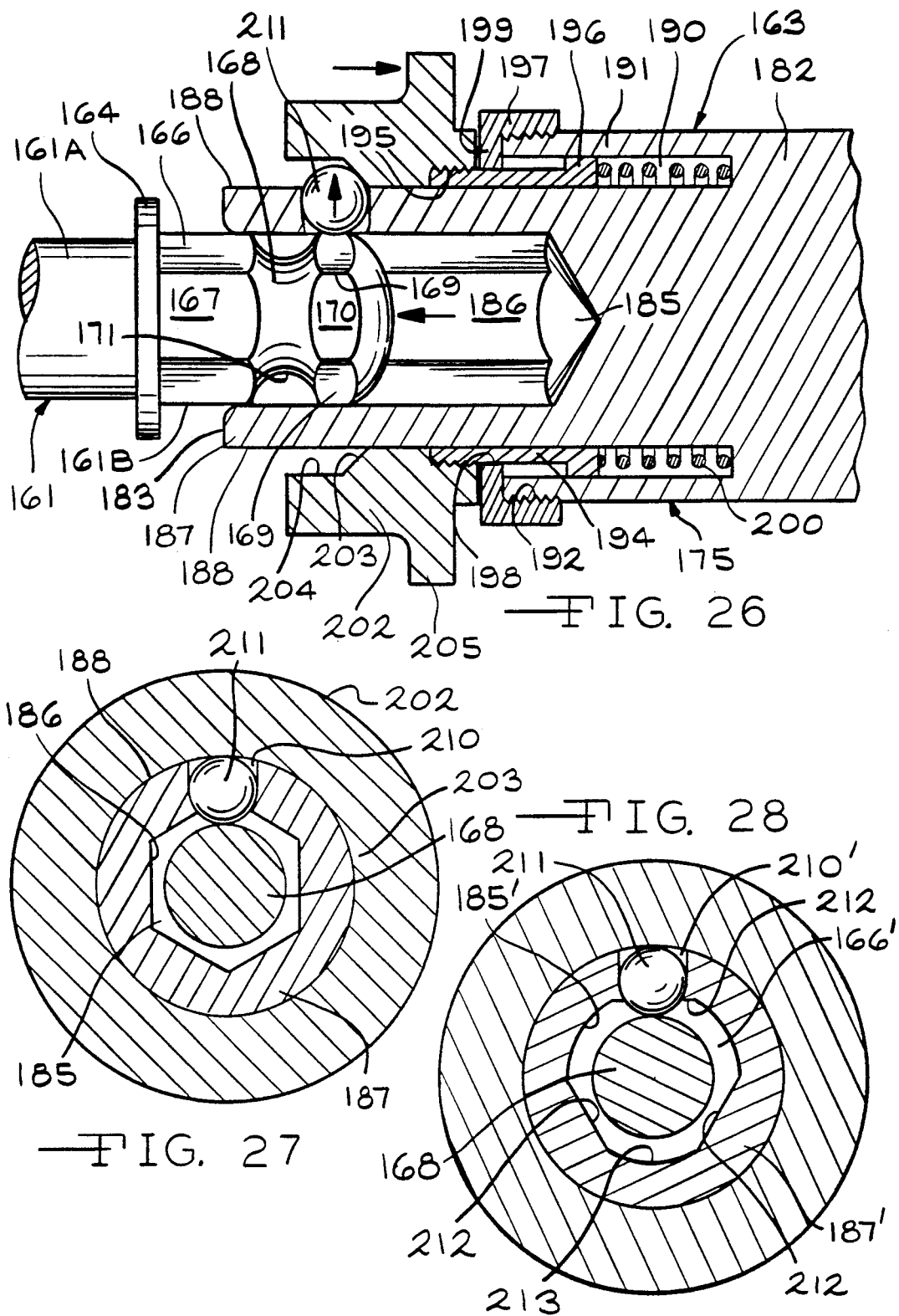

FEMORAL DISTRACTOR FOR USE IN KNEE SURGERY

CROSS REFERENCE TO RELATED APPLICATION

This is a continuation-in-part of application Ser. No. 07/871,036 filed Apr. 20, 1992 which is a division of application Ser. No. 07/508,090, filed Apr. 11, 1990 now U.S. Pat. No. 5,217,463.

BACKGROUND OF THE INVENTION

In performing knee surgery it is of the utmost importance to avoid or at least minimize damage to ligaments, tendons, muscles, nerves and other portions of the soft tissue while gaining access to and performing surgical procedures on various portions of bone structure of the knee. Heretofore, the retractors utilized in performing knee surgery have not been specifically tailored to permit maximum access to the bone structure intended for osteotomy procedures while at the same time providing maximum protection for various soft tissue members.

U.S. Pat. No. 4,820,797 discloses a collateral ligament retractor for use in knee surgery. Such retractor includes a member having a cupped arcuate finger for insertion into the knee joint along and partly around the tibial plateau and a curved portion extending from the finger outwardly around the ligament, then extending back substantially in the same direction as the finger and including a downwardly extending pivoted elongated arm extending to a position behind the knee above the calf. A second member of similar design but larger to accommodate the averted patella is positioned around the opposite ligament and a tension member such as a coil spring is connected to the outer end of the arms of the members for biasing them toward one another to hold the ligaments in a retracted position.

Patentschrift No. DD-215-46Y-A of the Duetsche Demokratische Republic discloses a wound retractor for knee surgery which has a holder having a hook-shaped convex blade at the distal end.

U.S. Pat. No. 2,695,607 discloses a surgical retractor intended to hold back flesh and muscles from a bone on which surgical treatment is to be performed.

Zimmer Company, Warsaw, Ind., Catalog for 1966 discloses on page 117 a Blount Knee Retractor having a handle with a tip disposed at an angle of more than 90° which is intended to be inserted into the knee joint just proximal to the cartilage so as to expose the line of dissection while broadening out to retract the superficial soft tissue without use of an additional retractor.

None of the retractors disclosed in the above referenced prior art or any other retractors known to the applicant have the capability of providing the degree of protection as those of the present invention and no prior art surgical procedures for knee surgery are as effective in permitting access to the bone structure upon which osteotomy procedures are to be performed while providing protection to the critical soft tissue.

SUMMARY OF THE INVENTION

The present invention relates to a method of performing knee surgery and to retractors and a femoral distractor for use in performing such surgery.

BRIEF DESCRIPTION OF THE DRAWINGS

FIG. 8 is a top plan view of the PCL tibial retractor.

FIG. 9 is a sectional view taken along line 9—9 of FIG. 8.

FIG. 10 is a top plan view of the lateral patellar retractor of the present invention.

FIG. 11 is an elevational view of the lateral patellar retractor as shown in FIG. 10.

FIG. 12 is a fragmentary plan view of the retracting end of the lateral patellar retractor shown in FIG. 10 with such end rotated for clarity.

FIG. 13 is a top plan view of the posterior cruciate ligament retractor of the present invention.

FIG. 14 is a side elevational view of the posterior cruciate ligament retractor as shown in FIG. 13.

FIG. 15 is a sectional view taken through line 15—15 of FIG. 14.

FIG. 16 is a top plan view of the collateral ligament retractor of the present invention.

FIG. 17 is an elevational view of the collateral ligament retractor as shown in FIG. 16.

FIG. 18 is a top plan view, partly in section, of the femoral distractor of the present invention.

FIG. 19 is an elevational view of the femoral distractor as shown in FIG. 18.

FIG. 20 is a sectional view taken through line 20—20 of FIG. 18.

FIG. 21 is a top plan view of the unicompartmental retractor of the present invention.

FIG. 22 is an elevational view of the unicompartmental retractor as shown in FIG. 21.

FIG. 26 is a view similar to FIG. 25 showing manipulation of the coupling in order to release it from engagement with the insertion rod.

FIG. 27 is a sectional view taken through line 27—27 of FIG. 25.

FIG. 28 is a view similar to FIG. 27 showing another embodiment.

BEST MODE FOR CARRYING OUT INVENTION

Figure 1:
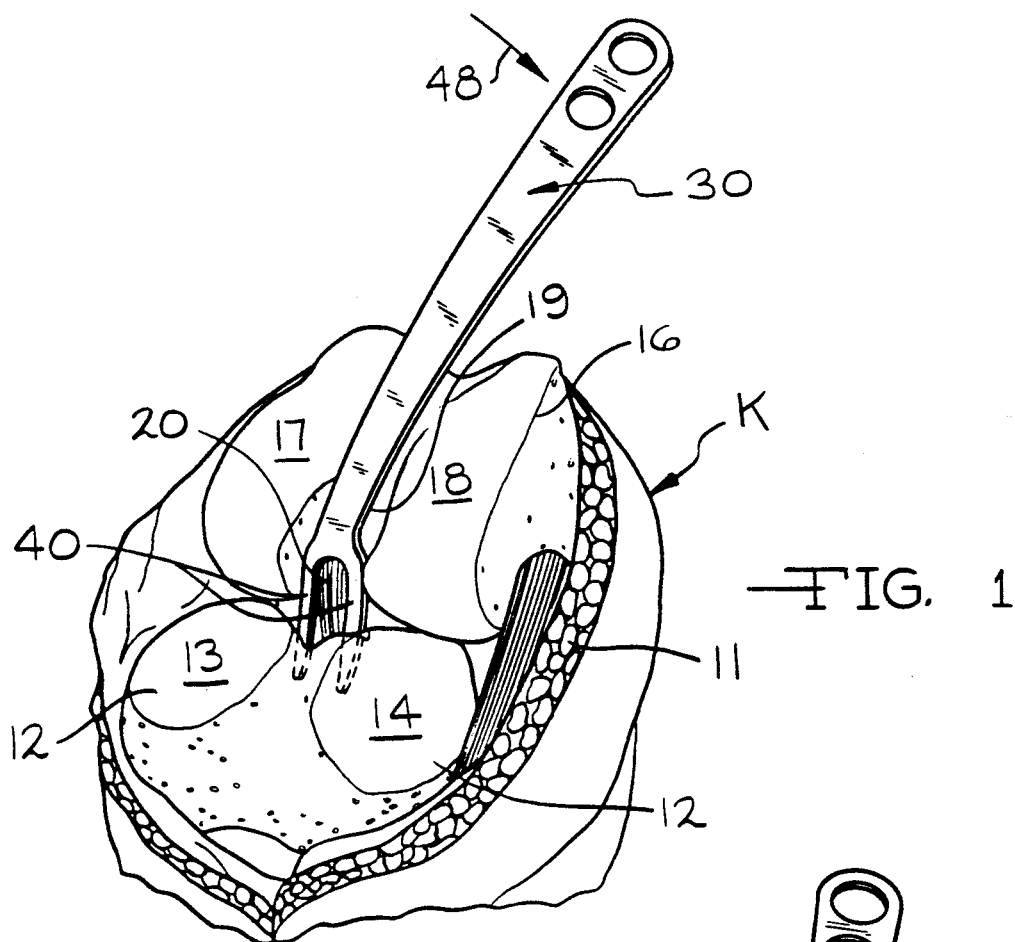
FIG. 1 is a perspective view showing a step in the knee surgery showing use of the PCL tibial retractor of the present invention.

Referring to FIGS. 1-7, there is shown a knee generally designated by the letter K in which an incision has been made through the skin and flesh 11 to expose the interior members upon which osteotomy and other procedures are to be performed. Such other procedures may include fitment and placement of an artificial knee prosthesis. Once such prosthesis is shown and described in the brochure published by Johnson & Johnson Orthopaedics, New Brunswick, N.J., in September 1988 entitled "P.F.C. TOTAL KNEE SYSTEM" ("P.F.C." is a registered trademark of Johnson & Johnson Orthopaedics Inc.) using a surgical technique described in a booklet published by Johnson & Johnson Products Inc. entitled "Surgical Technique—The Press Fit Condylar Total Knee System With Specialist Instrument". Although retractors will obviously be used throughout the entire surgical procedure of implanting any such prosthesis, the retractors and method defined by the present invention are directed primarily to preparation of various portions of the bone structure for receiving any such prosthesis and protection of the ligaments, tendons, muscles, nerves and other critical soft tissue members during osteotomy and other procedures.

As shown in FIGS. 1-7, the incision in the knee K permits access to the tibial plateau 12 including lateral and medial tibial condyles 13 and 14, respectively. With knee bent as shown in FIGS. 1-7 there is also exposed the distal femur 16 including lateral and medial femoral condyles 17 and 18, respectively. The intercondylar notch (femoral trochlear groove) 19 separates the lateral and medial femoral condyles 17 and 18, respectively. The posterior cruciate ligament 20 is attached to the femur and tibia proximally and distally, respectively, and needs to be completely protected during the osteotomy.

Figure 2:
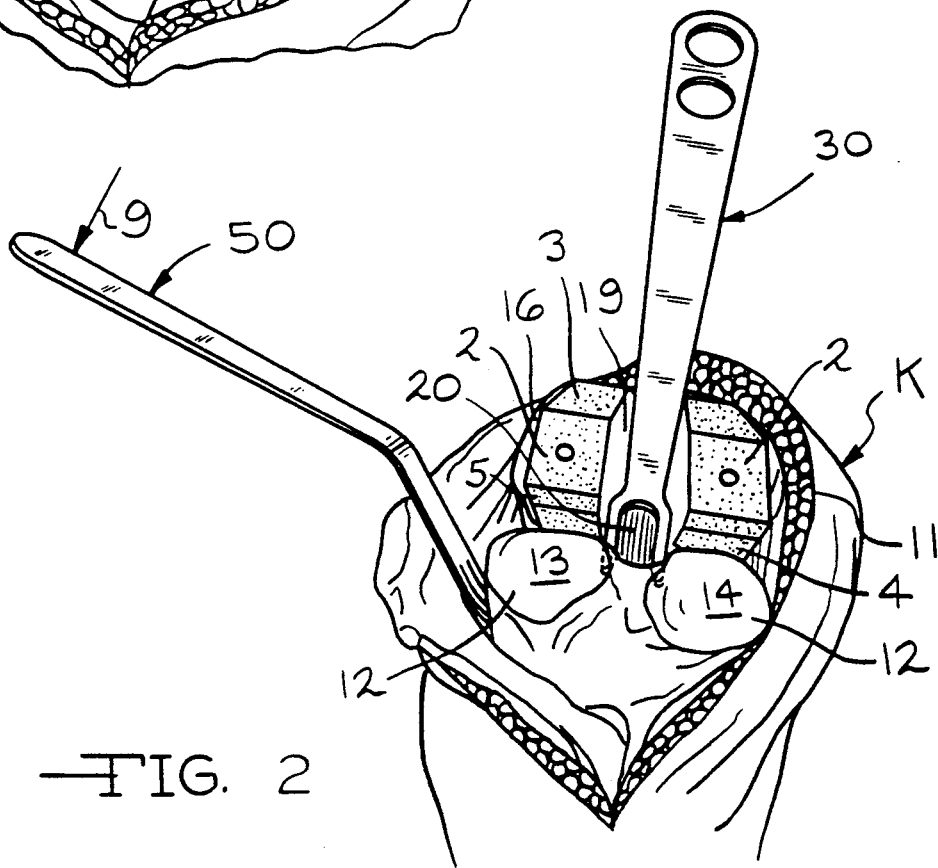
FIG. 2 is a perspective view similar to FIG. 1 showing the PCL tibial retractor and the lateral patellar retractor of the present invention in use during surgery.
Figure 3:
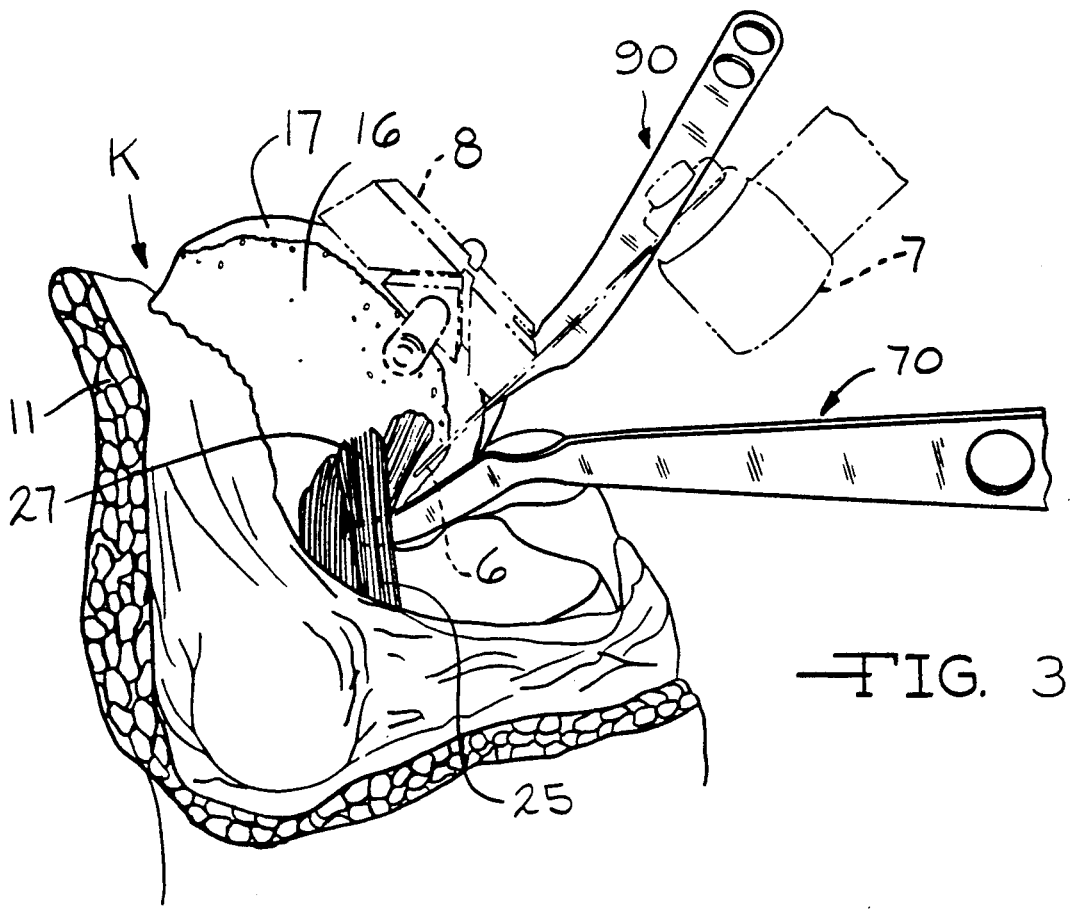
FIG. 3 is a perspective view looking from the side of a knee during surgery and showing the step of using a posterior cruciate ligament retractor and a collateral ligament retractor according to the present invention.
Figure 4:
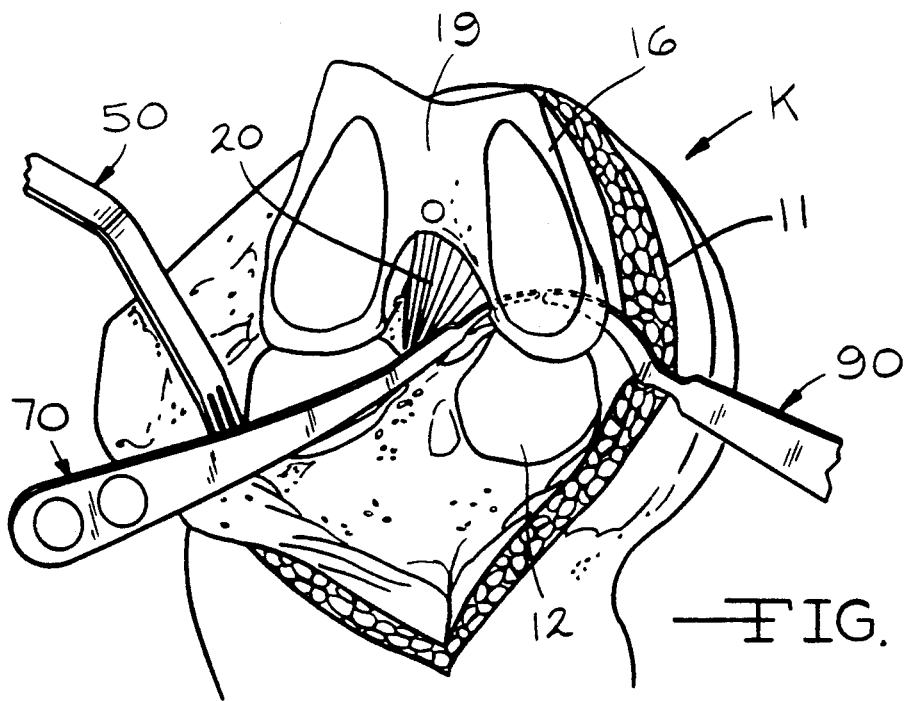
FIG. 4 is a perspective view taken from the front of a knee during surgery showing the step of using the lateral patellar retractor, the posterior cruciate ligament retractor and the collateral ligament retractor.
Figure 5:
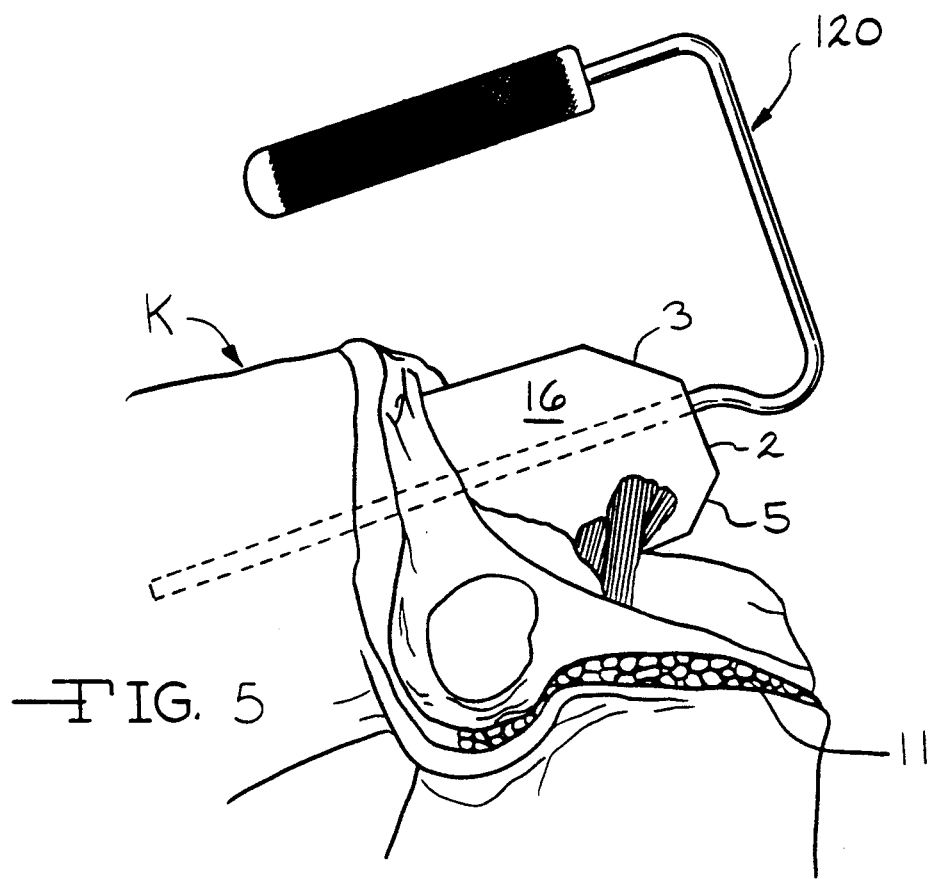
FIGS. 5 and 6 are perspective views from different angles showing the use of the femoral distractor portion of the present invention.
Figure 6:
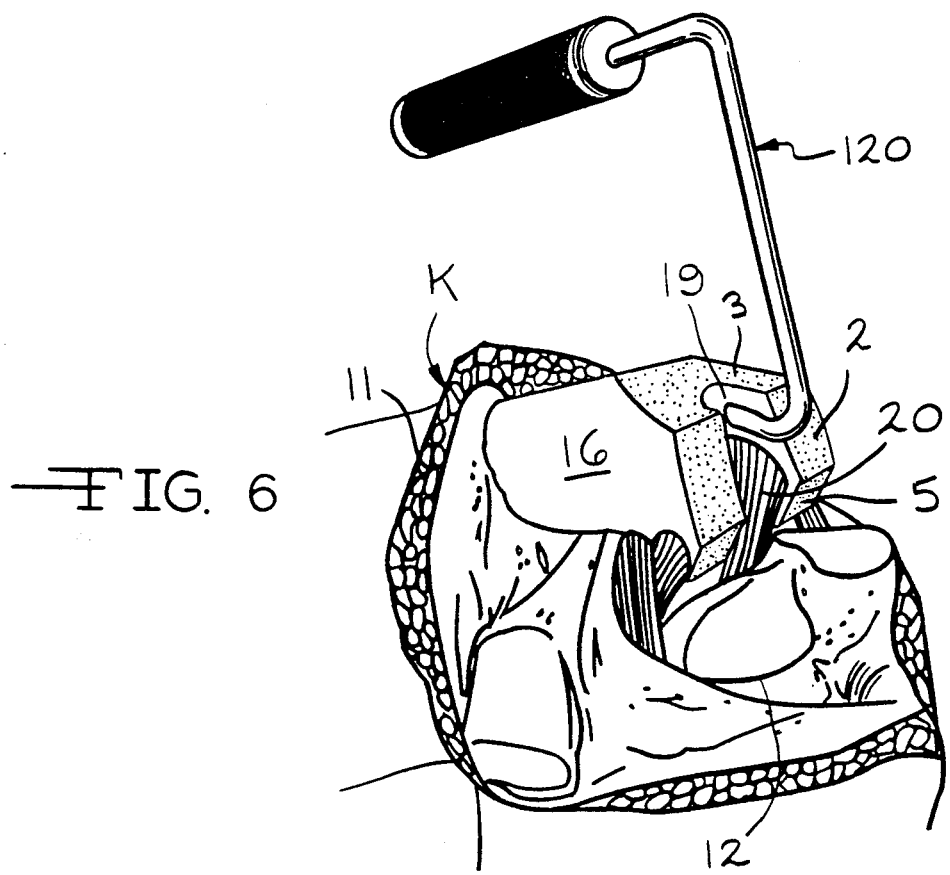
Figure 7:
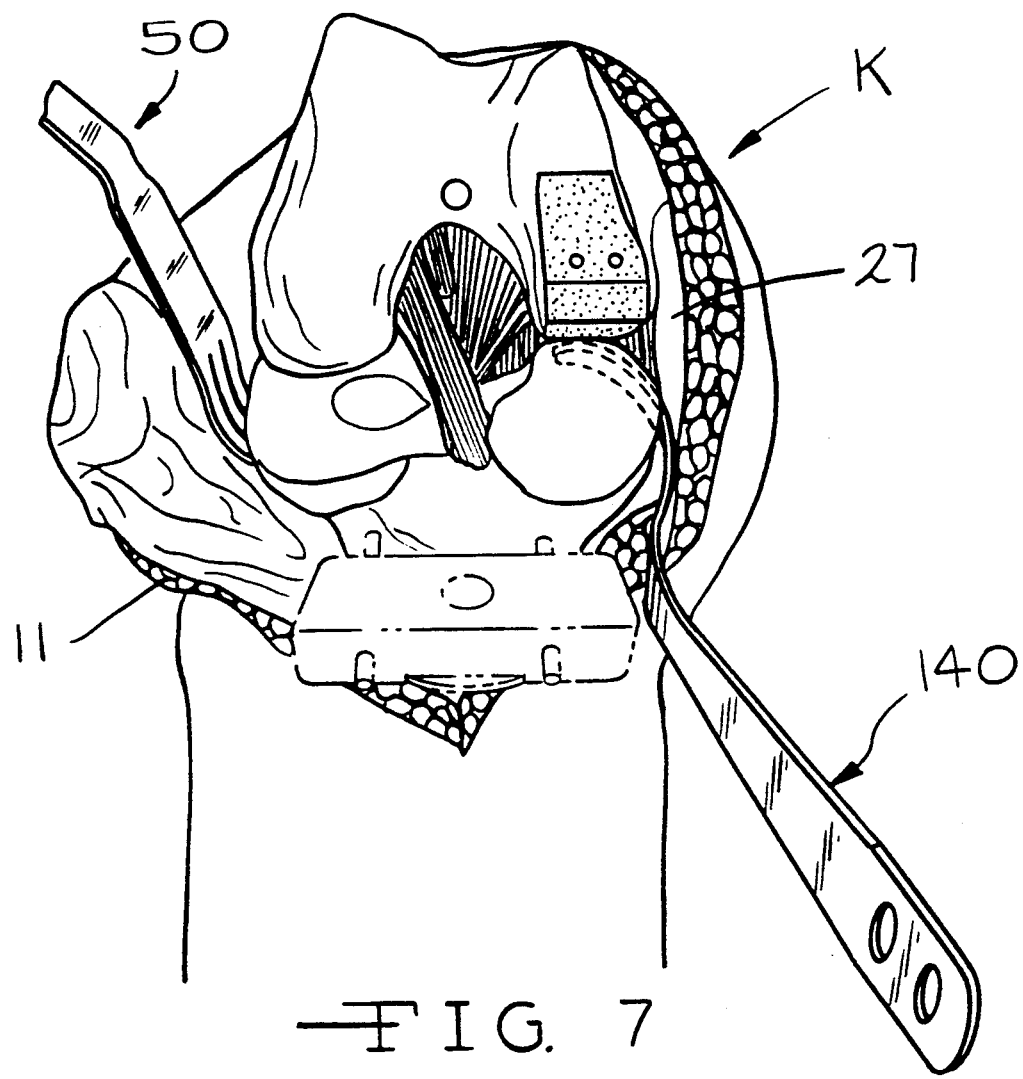
FIG. 7 is a perspective view taken from the front showing the step of using unicompartmental retractor in combination with the lateral patellar retractor.
Figure 23:
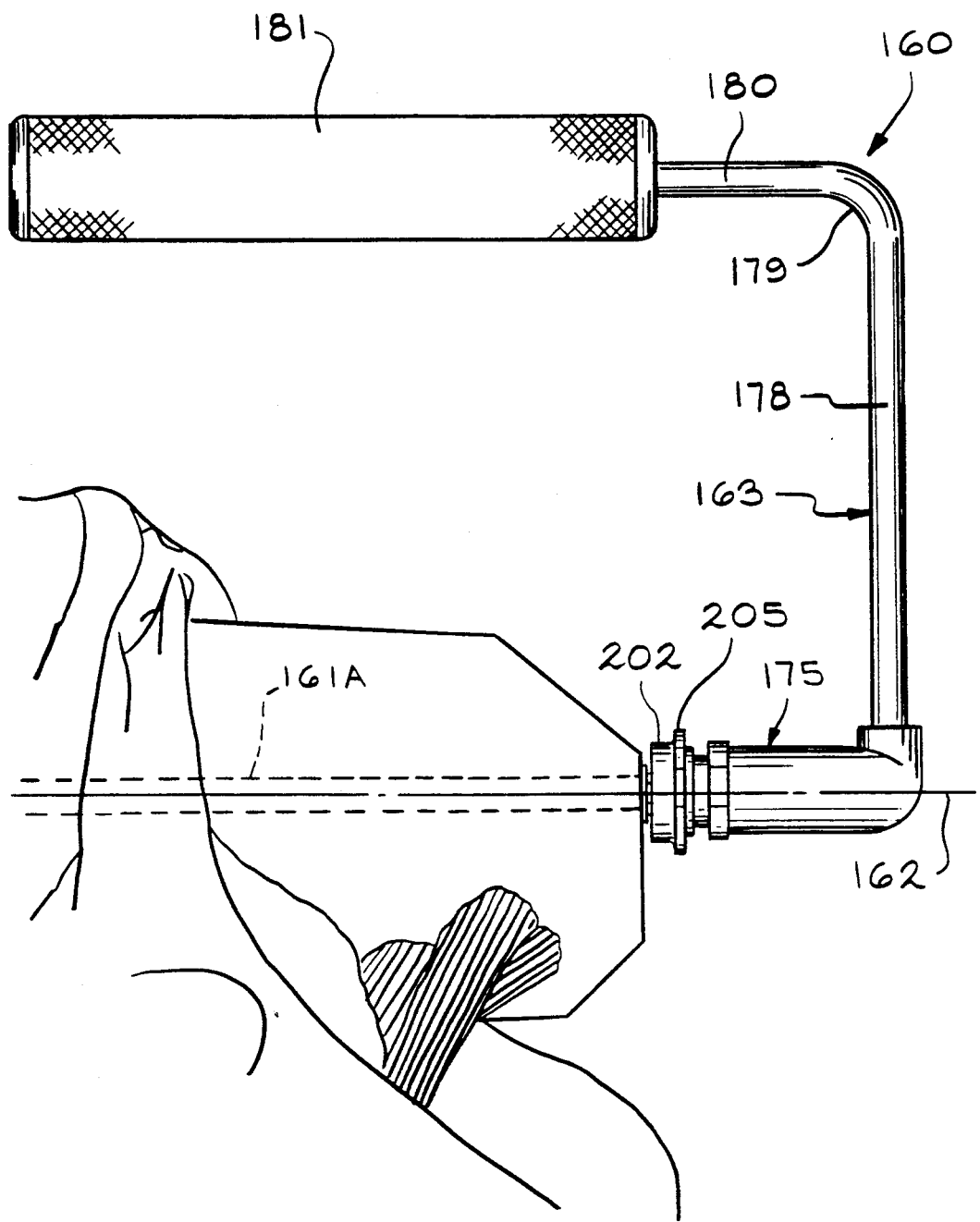
FIG. 23 is an elevational view of a modified femoral distractor shown in use during surgery.
Figure 24:
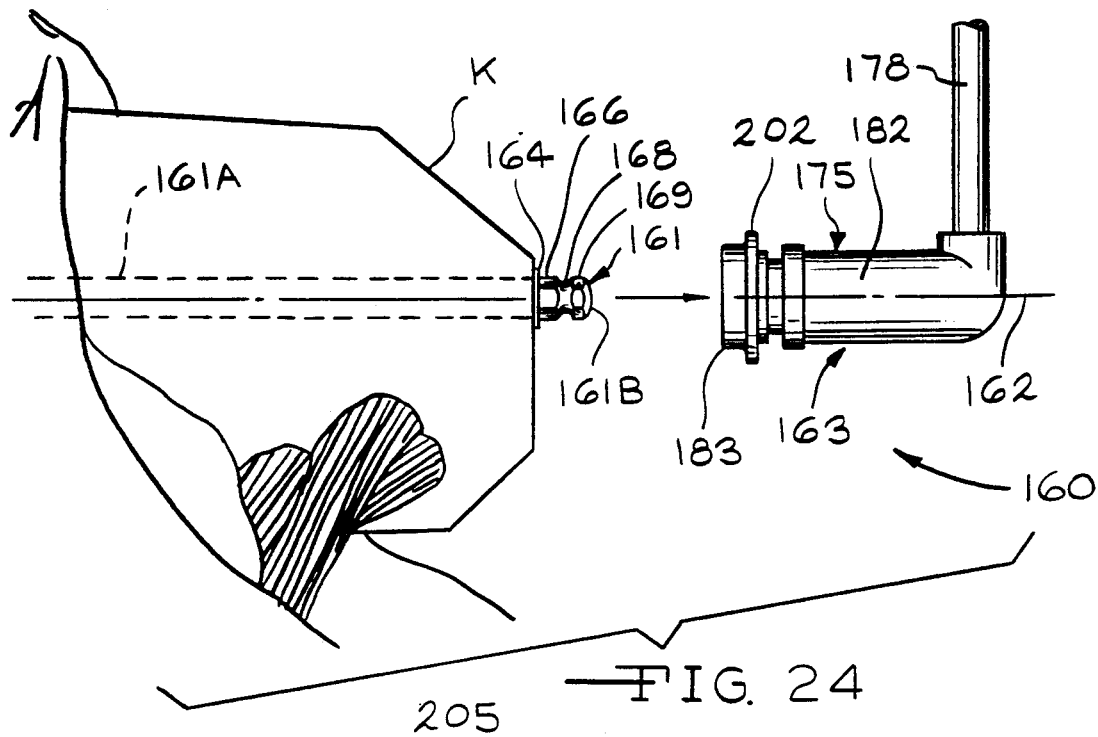
FIG. 24 is a view similar to FIG. 23 but showing a fragmentary portion of the handle following removal of the handle from the insertion rod.

FIGS. 2, 5 and 6 show the distal femur 16 following condylar osteotomies including distal femoral 2, anterior 3, posterior 4 and chamfer 5 cuts while FIG. 3 shows the position of the blade 6 of an oscillating saw 7, cutting guide 8 and PCL and collateral ligament retractors to be described hereinafter during posterior 4 femoral osteotomy. Also shown in FIG. 3 is the fibular (lateral collateral) ligament 25 which extends from the lateral aspect 27 of the lateral femoral condyle 17 to the head of the fibula (not shown). Additionally, as shown in FIG. 7, the collateral ligament 27, including its surrounding capsule is also exposed and needs to be protected during unilateral proximal tibial osteotomy.

Referring now to FIGS. 1, 2, 8 and 9, there is provided a PCL tibial retractor 30 which will be described as manufactured and as used in the surgical method herein. The PCL tibial retractor 30 includes a handle 31 which has generally flat upper and lower parallel surfaces 32 and 33, respectively, and edges 34 and 35 which taper inwardly toward each other and toward a longitudinal axis 36 from an area of maximum breadth adjacent an arcuate free end 37. The handle 31 may have one or more holes 39 to provide a place for hooking a weight thereto.

Integrally formed with the handle 31 is an integral support section 38 from which extend a pair of integral prongs 40. The support section 38 and prongs 40 will be described with the handle 31 oriented in a horizontal position. With the handle 31 so positioned, the support section 38 and prongs 40 will have an upper surface 32' and a lower surface 33' following a gentle S-shaped curve such that the support section 38 follows a curve 41 downwardly from horizontal and the prongs 40 follow a reverse curve 42 having a radius of curvature substantially the same as that of the support section and extending to ends 43 which are angled upwardly toward such horizontal plane at an angle of about $5° +/- 2°$. The lower surface 33' of the curved portion 41 has a radius of curvature of 3.312 inches $+/0.5$ inch with its center located 3.312 inches below the lower surface 33 of the handle 31 and 3.312 inches behind the ends 43. The upper surface 32' of the curved portion 42 has a radius of curvature of 3.312 inches $+/- 0.5$ inch with its center located 2.625 inches above the upper surface 32 of the handle 31 and 0.400 inch behind the ends 43. If desired, there could be a short planar segment separating the curved portion 41 from the reverse curve 42.

The PCL tibial retractor as shown in FIG. 9 has a uniform thickness of 0.120 inch throughout except for the last 0.5 inch of the prongs 40 adjacent the ends 43 each of which tapers to a thickness of 0.030 inch $+/- 0.010$ inch at the ends 43. The thickness and shape of the handle are not critical; however, the handle must be sufficiently rigid to prevent excessive bending during use and must have a shape which is convenient to use without obstructing desired surgical procedures when in use.

Referring now to FIG. 8, the support section 38 includes edges 34' and 35' which taper inwardly toward a vertical plane lying on the longitudinal axis 36 to a point of minimum breadth just before the juncture between the support section 38 and the prongs 40. This area should have a breadth of 0.430 inch $+/- 0.020$ inch in order that it can fit within the intercondylar notch 19 of the femurs and to use that portion as a fulcrum without damaging it. If desired, the support section 38 could have parallel edges 34' and 35' spaced apart such distance, in which case, such edges would flare outwardly at their respective junctures with the handle 31.

As can also be seen in FIG. 8, the edges 34' and 35' join with the outer edges 34" and 35", respectively, of the prongs 40. Such outer edges 34" and 35" follow a straight line path parallel to such vertical plane lying on the longitudinal axis 36 and are spaced apart 0.770 inch $+/- 0.020$ inch.

The prongs 40 have inner edges 48 and 49 which follow a straight line path in the area of juncture with said integral support section 38 and which taper outwardly from said vertical plane at an angle of 5° for the 0.5 inch portion adjacent the respective ends 43. The distance between the inner edges 48 and 49 in the straight line portion of the prongs is 0.430 inch $+/- 0.020$ inch. The ends 43 are rounded with the respective tips having a breadth of 0.030 inch $+/- 0.010$ inch. The inner edges 48 and 49 are joined by an arcuate segment 47, preferably having a radius of at least 0.215 inch.

As can be seen in FIGS. 1 and 2, the size, shape and space between the prongs 40 permit the prongs to straddle and thus protect the posterior cruciate ligament 20 and for the portions adjacent the ends 43 to rest against the posterior side of the respective lateral tibial condyle 13 and medial tibial condyle 14. The PCL tibial retractor 30 may then be moved in a direction toward the patient as indicated by the arrow 48 thus using the intercondylar notch 19 as a fulcrum. Such positioning presents the surfaces of the lateral tibial condyle 13 and medial tibial condyle 14 for osteotomy.

Referring now to FIGS. 2, 10, 11 and 12, there is shown a lateral patellar retractor 50 which includes a handle 51 having a longitudinal axis 56 and having generally flat upper and lower parallel surfaces 52 and 53, respectively, and edges 54 and 55. As may be seen in FIG. 10, the edges 54 and 55 are parallel to one another and to the longitudinal axis 56 in the area extending to an arcuate free end 57. The handle has one or more apertures 59 through which weighted hooks may be placed if it is desired to retain the retractor in position without a person attending thereto. Integrally formed with the handle 51 is a flat planar support section 58 which is disposed at an angle downwardly of approximately 55° from horizontal when the handle 51 is oriented in a horizontal position. Such angle could vary by as much as +/−30°. An arcuate section 61 joins the support section 58 to the handle 51.

Approximately one-third of the way between the free end 57 and the arcuate section 61, the edges 54 and 55 taper inwardly toward the longitudinal axis 56 at an angle of approximately 4°. The edges 54 and 55 continue to taper inwardly toward such longitudinal axis until they reach a point of minimum breadth 60. As can be seen in FIGS. 10 and 12, the support section 58 has edges 54' and 55' which are parallel to each other and to a vertical plane lying on the longitudinal axis. Preferably the distance between such edges is about 0.71 inch; however, since its function is primarily to move the incised soft tissue away from the lateral tibial condyle 13 (see FIG. 2), it could be broader or somewhat narrower and the edges 54' and 55' are not required to be straight.

Integrally formed with and extending from the support section 58 are three prongs including a pair of side prongs 63 and a center prong 64. As can be seen from the drawings, the center prong 64 extends beyond the ends of the two side prongs 63. The prongs 63 and 64 are joined to the planar portion of the support section 58 and, as may be seen in FIG. 11 have upper and lower surfaces 52" and 53" which initially follow a straight line path and terminate in an arcuate path. The arcuate path has a radius of 1.62 inch +/−0.5 inch to the upper surface 52" with a center located 1.19 inch below the plane defined by the upper surface 52 of the handle 51 and 0.54 inch beyond the end of the center prong 64. The segment of the prongs 63 and 64 following a straight line path is approximately 0.35 inch while the overall length of the side prongs 63 including the portion with the straight line segment is 1.07 inch +/−0.020 inch while the overall length of the center prong 64 is 1.32 inch +/−0.020 inch. Thus, the center prong 64 extends beyond the prongs 63 by 0.25 inch.

The side prongs 63 have outer edges 54" and 55" each of which, for about 0.35 inch, are extensions of and lie in the same path followed by the edges 54' and 55', respectively, of the adjacent portion of the support section 58. Each of the side prongs 63 has an inner edge 65 which, for about 0.35 inch, is parallel to the vertical plane extending through the longitudinal axis 56. The center prong 64 has a pair of edges 67, each of which, for about 0.35 inch, is spaced from and parallel to the first portion of the inner edges 65.

The end portions of each of the prongs 63 and 64 taper to rounded tips having a radius of 0.03 inch +/−0.010 inch in both the horizontal and vertical planes. Thus, as can be seen in FIG. 12, the edges 54" and 65; and 55" and 65 of each of the side prongs 63, for a distance of approximately 0.72 inch from their respective ends are disposed at an angle of approximately 16° to each other. Similarly, the edges 67 of the center prong 64 for a distance of approximately 0.97 inch from its end are disposed at an angle of approximately 16° to each other.

The distance between the outer edges 54" and 55" of the side prongs 63 is 0.71 inch +/−0.020 inch in the area parallel to the vertical plane extending through the longitudinal axis 56 with each of such prongs having a breadth in that area of 0.18 inch. The breadth of the center prong 64 in that area in which the edges 67 are parallel is 0.20 inch.

The thickness of the lateral patellar retractor 50 is 0.12 inches throughout the entire length except for the prongs 63 and 64 which taper at their ends to a thickness of 0.06 inch +/−0.010 inch. The taper in thickness for the side prongs 63 and center prong 64 begins at a point 0.35 inch from their respective junctures with the support section 58 as determined by the ends of the slots between the prongs. If desired, the lateral patellar retractor 50 could have four prongs with the two center prongs extending beyond the ends of the two side prongs.

As can be seen in FIG. 2, such construction permits the lateral patellar retractor 50 to be readily inserted along side of the lateral tibial condyle 13 so that the retractor 50 may use the shelve of such lateral tibial condyle 13 as its restive point. In as much as the center prong 64 is longer than the side prongs 63, the insertion may be easily accomplished. Such elongated center prong coupled with the curved upper and lower surfaces 52 and 53 at the ends of such center prong 64 and side prong 63 permit the lateral patellar retractor 50 to slide around the lateral tibial condyle with minimum damage to the surrounding soft tissue. In particular, such configuration clearly avoids damage to the common peroneal nerve, the tibial condyle itself or the attendant lateral soft tissue structures. The broad flat support section 58 engages the lateral soft tissue structure as the handle is moved in the direction indicated by the arrow 9. Thus, when the lateral patellar retractor 50 is in such position and the PCL tibial retractor 30 is positioned as described in FIG. 1 and as shown in FIG. 2, there is provided an unimpeded presentation of the tibial plateau 12 including the lateral tibial condyle 13 and medial tibial condyle 14 with the prepared distal femoral surface 16 held safely clear of the field to allow accurate tibial osteotomy.

Referring now to FIGS. 3, 4 and 13-17, there is shown a posterior cruciate ligament retractor 70 and collateral ligament retractor 90. The posterior cruciate ligament retractor 70 includes a handle 71 which has generally flat upper and lower parallel surfaces 72 and 73, respectively, and edges 74 and 75 which taper inwardly toward the each other and toward a longitudinal axis 76 from an area of maximum breadth adjacent an arcuate free end 77. The handle 71 may have one or more holes 89 to provide a place for hooking a weight thereto. The handle 71 merges into an integral support section 78 having edges 74' and 75'. The edges 74' and 75' are parallel to a vertical plane passing through the longitudinal axis 76 assuming that the portion of the handle 71 in the area of the free end 77 is in a horizontal position.

As can be seen from FIG. 15, the support section 78 has upper and lower surfaces 79 and 80, respectively, each of which has an arcuate configuration extending from edge 74' to edge 75'. Such arcuate configuration is not critical and one or both of such surfaces 79 and 80 could be flat. The distance between the edges 74' and 75' of the integral support section 78 is 0.43 inch +/−0.020 inch and the thickness in the center of such support section 78 and the handle 71 is about 0.12 inch. The thickness and shape of the handle 71 and support section 78 are not critical; however, they must be sufficiently rigid to prevent excessive bending during use and must have a shape which functions to retract and protect the appropriate soft tissue without obstructing desired surgical procedures when in use.

The handle 71 curves downwardly in an arcuate path with the lower surface 73 extending through an arc of 22° with a radius of 5.0 inch+/−0.5 inch. The integral support section 78 extends in a generally straight line path downwardly at an angle of 22°+/−1.5° from horizontal.

A tip 81 is integrally formed with and extends from the integral support section 78 to an end 84. The tip 81 has upper and lower surfaces 82 and 83 which follow an arcuate path reversed from the arcuate path of the handle 71 with the upper surface 82 having a radius of 2.0 inch+/−0.4 inch with a center of radius located 0.78 inch above a plane defined by the upper surface 72 of the handle 71 and approximately 0.18 inch behind the end 84 of the tip 81. The length of the tip 81 from the support section 78 to the end 84 is 1.10 inch+/−0.020 inch. The end 84 and the portion of the tip 81 adjacent thereto are angled upwardly toward horizontal. The tip 81 has edges 85 and 86 which taper at an angle of 4°+/−1° to a vertical plane passing through the longitudinal axis (included angle equals 8°+/−2°). Each of the edges 85 and 86 flares outwardly through arcuate sections 87 and 88, respectively, in the area where the tip 81 merges with the support section 78. The edges 85 and 86 extend to the end 84 which is defined by an arcuate path having a radius of 0.05 inch+/−0.01 inch.

The thickness of the tip 81 tapers from 0.12 inch at the support section 78 to 0.045 inch+/−0.010 inch at the end 84. The end is rounded from the lower surface 83 to the upper surface 82 with a radius of 0.04 inch+/−0.01 inch.

Referring now to FIGS. 16 and 17, the collateral ligament retractor 90 includes a handle 91 which has generally flat upper and lower parallel surfaces 92 and 93, respectively, and edges 94 and 95. The edges 94 and 95 are generally parallel in the area adjacent an arcuate free end 96. The handle 91 may have one or more holes 109 to provide a place for hooking weights thereto. At any desired point, the edges 94 and 95 taper toward a longitudinal axis 97. The handle 91 merges into an integral support section 98. The integral support section 98 includes upper and lower surfaces 99 and 100, respectively, which curve downwardly following a curved path through an arc of approximately 28° on a radius of approximately 1.25 inches from the lower surface 100. The support section 98 has edges 101 and 102 which follow a straight line path parallel to a vertical plane passing through the longitudinal axis 97 and flare outwardly where they are joined to edges 94 and 95, respectively, of the handle 91. The breadth of the support section 98 in the area in which the edges 101 and 102 follow a straight line path is 0.24 inch+/−0.020 inch.

A tip 103 extends from the integral support section 98 to a blunt free end 106. The tip 103 has upper and lower surfaces 104 and 105, respectively, which follow a curved path through an arc of 44.5°+/−0.5° and having a radius of 3.0 inches, the center of which is 2.5 inches+/−0.5 inch above a horizontal plane defined by the upper surface 92 of the handle and positioned 0.88 inch behind the end 106 of the tip 103. Thus, as can be seen, the tip 103 has its end 106 pointed slightly upwardly toward the horizontal plane defined by the upper surface 92; however, it does not extend up to such plane. At its lowest point, the tip 106 is approximately 0.59 inch below such horizontal plane.

The tip 103 has edges 107 and 108, respectively, which taper inwardly toward a vertical plane passing through the longitudinal axis 97 at an angle of 4°+/−1° and joining the end 106 which has a radius of 0.125 inch+/−0.010 inch. Thus the included angle between the edges is 8°+/−2°. The tip 103 has a maximum breadth 0.41 inch+/31 0.02 inch located 1.93 inch from the end 106. The breadth near the end 106 at the point of juncture between the straight line segment of the edges 107 and 108 and the arcuate tip is 0.25 inch+/−0.02 inch.

The collateral ligament retractor 90 has a thickness of 0.12 inch throughout the handle portion 91 and the integral support section 98 and tapers to a thickness of 0.09 inch+/−0.02 inch at the end 106 with the end rounded in the vertical direction on a radius of 0.045 inch+/−0.01 inch. The thickness and shape of the handle 91 and the thickness of the support section 98 are not critical; however, they must be sufficiently rigid to prevent excessive bending when in use and must have a shape which functions to retract and protect the appropriate soft tissue without obstructing surgical procedures when in use.

Referring now to FIGS. 5, 6 and 18–20, there is shown a femoral distractor 120 for use in providing traction to the femur during surgery. Such distraction opens the joint to enhance visualization of the posterior capsule and facilitate removal of osteophyte, loose bodies and residual meniscal tissue. Such distraction also assists in accurate evaluation of the flexion gap. The femoral distractor 120 of the present invention permits the surgeon to provide maximum traction with minimized possibility of damage and ease of insertion into the medullary canal of the femur and includes vent means provided to relieve pressure during such insertion.

The femoral distractor 120 includes an insertion rod 121 following a straight line path along a longitudinal axis 122, a generally U-shaped support rod 123 integrally formed therewith and a handle 124 joined to support rod 123 along a second longitudinal axis 125 parallel to and spaced from the longitudinal axis 122.

The insertion rod 121 may have a circular cross-sectional configuration but preferably has a cross-sectional configuration such as that shown in FIG. 20, which can best be described as a circular cross-sectional configuration from which a chordal segment has been removed to provide a flat planar surface 126 in the area facing toward the handle 124.

The insertion rod 121 is also provided with a longitudinal groove 127 extending parallel to the longitudinal axis 122 from a rounded free end 128 to the juncture of the insertion rod 121 with the support rod 123. The groove 127 is positioned opposite the flat planar face 126 and provides a vent passageway to relieve pressure as the insertion rod is inserted into the medullary canal of the femur.

A significant feature of the femoral distractor 120 of the present invention resides in the configuration of the support rod 123 in the area of its juncture with the insertion rod 121. Thus, as shown most clearly in FIG. 18, a major portion 123A of the support rod 123 is disposed at an angle of 90° to the respective longitudinal axes 122 and 125. The portion forming the corner 123B initially follows an arcuate path in a direction away from both of said longitudinal axes 122 and 125 followed by a reverse curved portion joining it to the major portion 123A. Such construction permits the surgeon to apply the needed pressure required for maximum distraction under the circumstances while ensuring against undue pressure being placed against that portion of the femur adjacent the entry point of insertion into the medullary canal. Thus, construction of the support rod 123 with the outwardly bent corner 123B which initially extends away from the longitudinal axis 125 on which the handle is placed appears to provide for a more uniform distribution of the stresses over a large portion of the femur during distraction. In contrast, a distractor which follows a simple arcuate 90° path from the insertion rod to the support rod appears to concentrate excessive pressure at that portion of the femur immediately adjacent the point of insertion into the medullary canal. Such excessive pressure may also occur when distraction is performed by lifting the protruding end of a straight insertion rod which had been placed in the medullary canal.

Referring now to FIGS. 7, 21 and 22, there is provided a unicompartmental retractor 140 which is designed as a shield to protect the collateral ligament 27 and posterior structures during unilateral proximal tibial osteotomy.

The unicompartmental retractor includes a handle 141 which has generally flat upper and lower parallel surfaces 142 and 143, respectively, and edges 144 and 145. The edges 144 and 145 are generally parallel in the area adjacent an arcuate free end 146. The handle 141 may have one or more holes 147 to provide a place for hooking weights thereto. At any desired point, the edges 144 and 145 may taper toward a longitudinal axis 148.

Extending from the handle is an integral tip 150 having edges 144' and 145' which continue to taper toward a vertical plane passing through the longitudinal axis 148 (assuming the handle 141 is positioned with the upper and lower surfaces 142 and 143 in a horizontal plane). The tip 150 has upper and lower surfaces 142' and 143', respectively, which initially follow a straight line angled path downwardly from the handle 141 at an angle of approximately 45°+/−1.5°. It then joins with an arcuate portion where it curves upwardly on a radius of 1.5 inches+/−0.2 inch. The center of radius of such arc is positioned 0.35 inch+/0.2 inch above the plane defined by the upper surface 142 of the handle and 2.26 inches+/−0.05 inch forward of the juncture of the tip 150 with the handle 141. The arcuate section of the tip 150 has extending therefrom a short straight segment 151, 0.30 inch+/−0.02 inch in length, which is disposed at an angle of 5°+/−2° from vertical in a direction away from said handle 141 and terminates in an end 152 approximately 0.10 inch below the plane of the upper surface 142. The end 152 has a breadth of 0.30 inch+/−0.020 inch and preferably is rounded from the surface 142' to the surface 143'.

The handle 141 and the tip 150 up to approximately its lowest point of the arcuate section have a thickness of approximately 0.12 inch. However, the thickness in that area is not critical provided it is rigid enough to prevent excessive bending during use. From such lowest point to the end the thickness of the tip 150 tapers with a thickness at the end 152 of 0.060 inch+/−0.020 inch.

The angle of taper of the edges 144' and 145' is 5°+/−1° from a vertical plane passing through the longitudinal axis 148 for a total included angle of 10°+/−2.

In conducting the surgical procedure according to the method of the present invention, following incision of the knee K, the PCL tibial retractor 30 is inserted carefully between the distal femur 16 and the tibial plateau 12 with the prongs straddling on opposite sides of the posterior cruciate ligament 20 with the ends 43 of the prongs 40 resting against the posterior side of the lateral tibial condyle 13 and medial tibial condyle 14, respectively. The support section 38 of the PCL tibial retractor rests against the intercondylar notch 19 which acts as a fulcrum as the handle 31 is moved in the direction indicated by the arrow 48.

The lateral patellar retractor 50 is then inserted using the elongated center prong 64 as the lead along the lateral aspect of the lateral tibial condyle 13 with the support section 58 moving the adjacent soft tissue away from the incision to permit tibial osteotomy without risking damage to the surrounding soft tissue.

After performing osteotomy on the tibial plateau, namely, the lateral tibial condyle 13 and medial tibial condyle 14, the posterior cruciate ligament retractor 70 is inserted on the medial side of the medial femoral condyle 18 while the collateral ligament retractor 90 is passed around the opposite side of such medial femoral condyle 18 meeting posteriorly to form a protective arc to protect the ligaments and hold them clear of the blade of the oscillating saw during osteotomy of the posterior portion of the medial femoral condyle 18. The instruments are reversed and placed around the lateral femoral condyle 17 during posterior osteotomy of such lateral femoral condyle.

The unicompartmental retractor 140 is inserted around the side and posterior aspect of the tibial condyle, either the lateral tibial condyle 13 or medial tibial condyle 14, in order to protect the collateral ligament and posterior structures during unilateral proximal tibial osteotomy.

Referring now to FIGS. 23-28, there is shown a modified femoral distractor 160 which includes an insertion rod 161 and handle assembly 163 having means for engagement with and disengagement from the insertion rod 161. The insertion rod 161 includes an insertion end 161A and a connector end 161B. The insertion end 161A follows a straight line path along a longitudinal axis 162 and is sized to permit insertion in the medullary canal of the femur when the knee K is in a position of flexion. As with the insertion rod 121 of the previous embodiment of femoral distractor 120, the insertion end 161A may have a circular cross-sectional configuration but preferably has a cross-sectional configuration such as that shown in FIG. 20 with respect to the insertion rod 121.

The connector end 161B includes a flange 164 extending radially outwardly from the insertion end 161A, and a first section 166 having a series of flats 167 extending parallel to the longitudinal axis 162 and defining a hexagon in cross section. A second section 168 of reduced cross-sectional size extends from the first section and a third section 169 having a size and cross-sectional configuration similar to that of the first section 166 extends from the second section 168. The third section 169 has a series of flats 170 which define, in cross section, a hexagon. The reduced cross-sectional size of the second section 168 results in an annular groove 171 between the first section 166 and third section 169. A dome 172 defines the end of the connector end 161B.

The handle assembly 163 includes a coupling member 175 extending along longitudinal axis 162, a support rod 178 extending from said coupling member 175, preferably at right angles to the longitudinal axis 162. The support rod 178 extends to a corner 179 (FIG. 23) from which extends a support section 180 having a gripping member 181 secured thereto. Preferably, the support section 180 and gripping member 181 are disposed at right angles to the support rod 178 and are parallel to the longitudinal axis 162 of the insertion rod 161.

The coupling member 175 includes a main body portion 182 and a wall 187 having a first end 183 extending therefrom. The wall 187 encircles a recess 185 extending along the longitudinal axis 162. The recess 185 is machined to define a series of flats 186 defining a hexagonal cross-sectional configuration and sized to slidingly receive therein the first and third sections 166, 169, with their respective flats, 167, 170, slidingly engaging the flats 186 of the recess. The recess 185 is sufficiently deep to permit the first and third sections 166 and 169 to be completely inserted therein. As will be appreciated, the engagement of the flats 167, 170, of the first and third sections 166, 169, with the flats 186 of the recess 185 effectively prevents rotation of the main body portion 182 relative to the insertion rod 161.

The wall 187 has a cylindrical exterior surface 188, the diameter of which is less than the diameter of the main body portion 182. The main body portion 182 is machined to form an annular slot 190 defined by a cylindrical wall 191 encircling the cylindrical exterior surface 188. As can be seen from FIGS. 25 and 26, the free end of the cylindrical wall 191 has threads 192 formed on the exterior surface thereof.

A sleeve member 194 is slidably engaged to the cylindrical exterior surface 188. One end of the sleeve member 194 has threads 195 formed thereon while the other end has an enlarged flange 196 which fits within and closes off the annular slot 190. An end cap 197 having a central opening 198 defined by a radially inwardly extending flange 199 is threadedly engaged to the threads 192 of cylindrical wall 191. The sleeve member 194 is slidably engaged to the cylindrical exterior surface 188 but has its flange 196 retained within the annular slot 190 by the flange 199 of end cap 197 as can be seen from FIG. 25.

Figure 25:
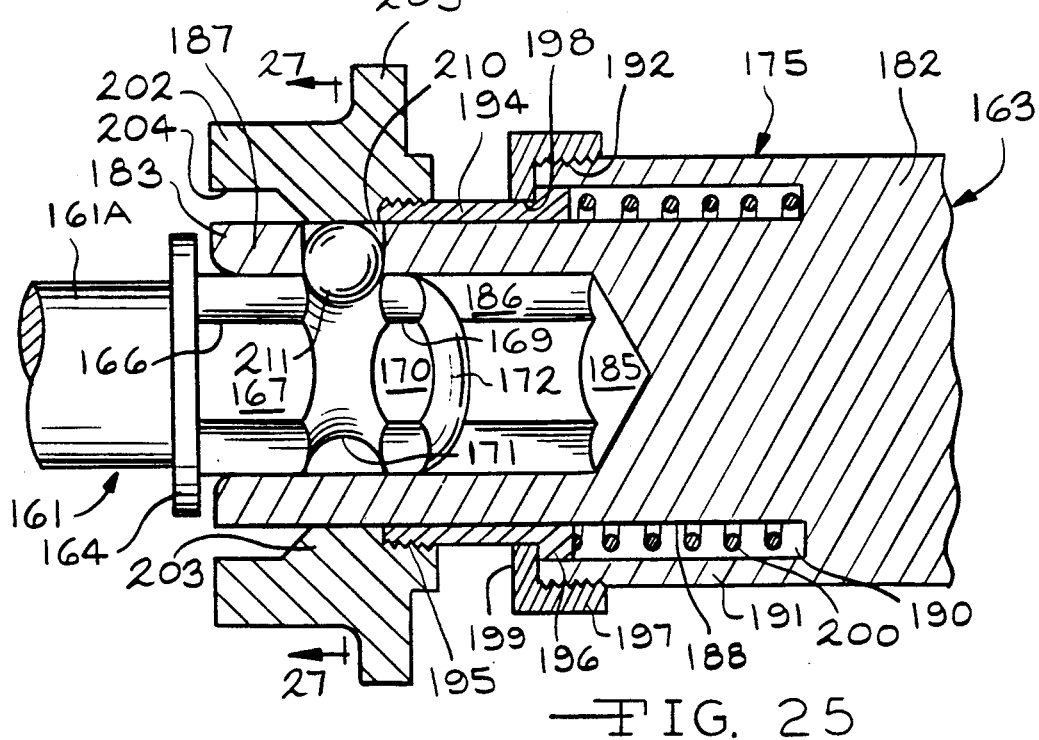
FIG. 25 is a fragmentary view showing, in section, the coupling portion of the detachable handle engaged to the insertion rod.

A compression spring 200 is positioned in the annular slot 190 and serves to yieldingly urge the sleeve member 194 to the position shown in FIG. 25.

Threadedly engaged to the threads 195 of sleeve 194 is a latch sleeve 202 having an abutment 203 which is also slidably engaged to the cylindrical exterior surface 188. The latch sleeve 202 is provided with a recessed area 204 adjacent the abutment 203 at its end opposite the threaded end. Additionally, it is provided with a radially outwardly extending finger flange 205 in the area of the threaded end.

The wall 187 is provided with one or more apertures 210. A detent ball 211 is positioned in the aperture 210. The aperture 210 is sized to receive the detent ball 211 at the cylindrical exterior surface 188 but has a reduced size smaller than the diameter of the detent ball 211 at the inner surface defined by the flats 186. The reduced size of the aperture at the side of the wall 187 prevents the detent ball 211 from escaping inwardly into the recess 185. The size of the aperture 210 at the interior of the wall 187 is just slightly smaller than the diameter of the detent ball 211 so that a significant portion of the detent ball 211 may move beyond the interior surface and fit within the annular groove 171 when the connector end 161B is positioned with the first, second and third sections 166, 168 and 169 in the recess 185. Thus, as can be seen in FIG. 25, when the connector end 161B is so positioned, the detent ball 211 is engaged within the annular groove 171 firmly retaining the connector end 161B to coupling member 175.

When it is desired to release the connector end 161B from the coupling member 175, it is necessary simply for the surgeon to engage the finger flange 205 and push the latch sleeve 202 to the right from the position shown in FIG. 25 to the position shown in FIG. 26 such that the recessed area 204 will be aligned with the detent ball 211. The detent ball is then free to move radially outwardly as shown in FIG. 26, thus removing the interference between it and the third section 169 and permitting the insertion rod connector end 161B to be removed from the coupling member 175.

Referring now to FIG. 28, there is shown another embodiment utilizing the detent ball 211 for retaining the handle on the insertion rod. This embodiment is similar to the embodiment of FIGS. 23-27 with two exceptions. The first is that in place of a recess 185 having a series of flats 186 defining a hexagonal cross-sectional configuration, there is provided a recess 185' which has three flat walls 212 separated by three arcuate walls 213. The second is that the first section 166' and the third section (not shown) of the insertion rod connector end have cross-sectional configurations identical to that of the recess 185' and are sized to permit ready insertion thereof into such recess 185'. As will be appreciated, the flat walls 212 engaging similar flat walls on the first section 166' and third section (not shown) will prevent rotation of the coupling member relative to the engaged insertion rod.

Figure 29:
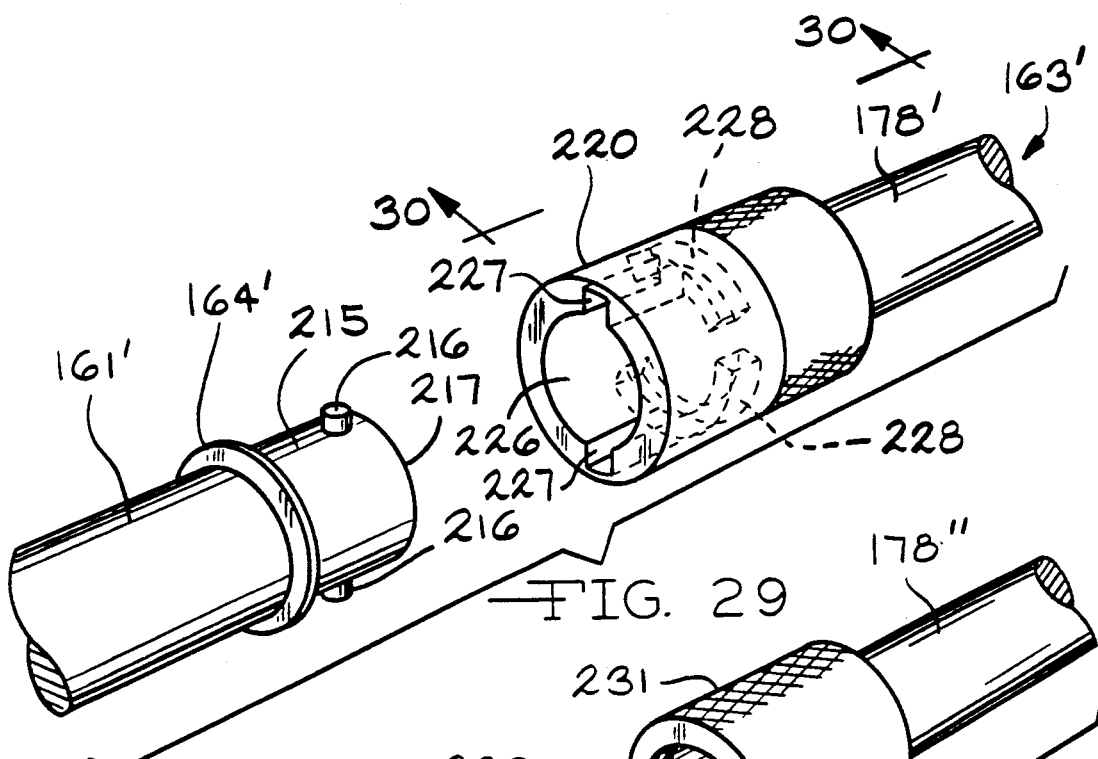
FIG. 29 is an exploded fragmentary view showing a modified coupling for connecting the detachable handle to the insertion rod.
Figure 30:
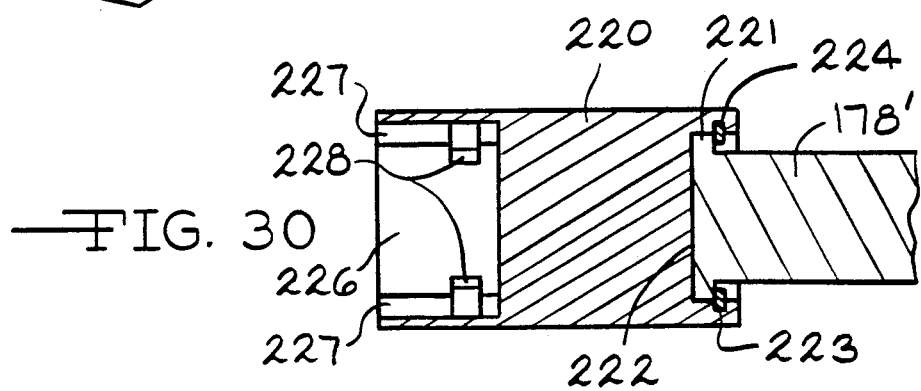
FIG. 30 is a sectional view taken through line 30—30 of FIG. 29.

Referring now to FIGS. 29 and 30, there is shown modified design for engaging the coupling member to the insertion rod. Under this embodiment, the insertion rod 161' has a radially outwardly extending flange 164' from which extends a cylindrical stub 215 having a pair of oppositely positioned radially outwardly extending bayonets 216 spaced a short distance from the free end 217 of the cylindrical stub 215.

In this embodiment the handle assembly 163' is provided with a bayonet-type coupling member 220 which is rotatably connected to the support rod 178'. The support rod 178' has a radially outwardly extending flange 221 at its end. (See FIG. 30). The coupling member 220 is provided with a recess 222 sized to receive the flange 221. An annular groove 223 is formed in the wall of the coupling defining the recess 222. A split ring 224 is snapped in the annular groove 223 and engages the flange 221 thus retaining the coupling member 220 to the support rod 178'.

The opposite end of the coupling member 220 is provided with a recess 226 having a pair of oppositely disposed longitudinal slots 227 sized to receive the bayonets 216 when the cylindrical stub 215 is inserted in the recess 226. The slots 227 extend to the bottom of the recess 226 and communicate with arcuate slots 228 which will receive the bayonets 216 upon rotation of the coupling member 220 relative thereto. As can be seen in FIG. 29, the arcuate slots 228 extend in both directions from the longitudinal slots 227. As a result, the coupling member 220 may be engaged to the stub 215 and bayonets 216 by rotating it in either a clockwise or counterclockwise direction.

Figure 31:
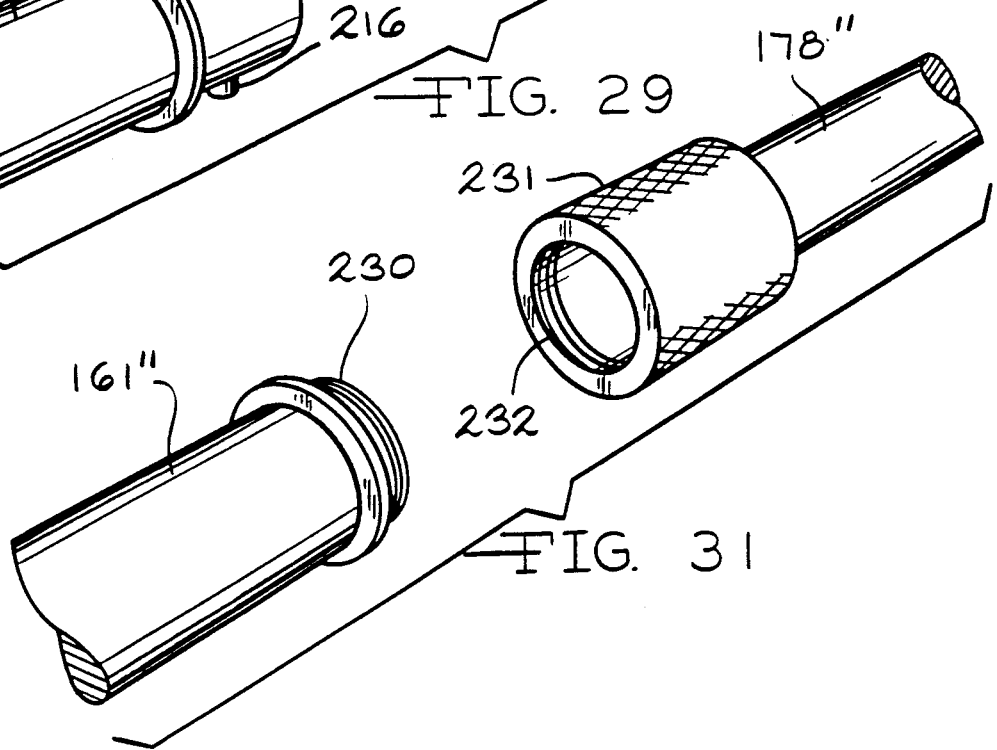
FIG. 31 is a view similar to FIG. 29 showing another embodiment of coupling means for connecting the detachable handle to the insertion rod.

Referring now to FIG. 31, there is provided an insertion rod 161'' which has a series of threads 230 at its end. In this embodiment the coupling member 231 is rotatably engaged to support rod 178'' and is provided with threads 232 which engage the threads 230 of the insertion rod 161'' upon rotation of the coupling member therewith.

As previously mentioned with respect to the description of FIGS. 5, 6 and 18–20, the use of a femoral distractor to provide traction to the femur during surgery not only enhances visualization of the posterior capsule and facilitates removal of osteophyte, loose bodies and residual meniscal tissue, such distraction also assists in accurate evaluation of the flexion gap. This is important in determining the correct sizes of the various components of the prosthesis being implanted and is particularly relevant with respect to insertion of tibial trials when the femoral trial remains in place. The size of the flexion gap determines the thickness of the tibial insert to be mounted on the tibial base implant to insure the proper engagement of the femoral implant with the tibial insert implant. Thus, depending upon a number of factors, including the amount of bone removed in preparation, it may be desirable to use a tibial insert having a thickness rated as thin as 8 mm or as thick as 20 mm. See for example, a brochure copyrighted 1989 by Dow Corning Wright entitled "Whiteside Ortholoc ® Modular Knee System—Total Condylar" and a brochure copyrighted 1988 by DePuy ® Division of Boehringer Mannheim Corporation, Warsaw, Ind. In order to determine the appropriate thickness of insert, it is desirable to move the leg between positions of flexion and extension. As will be appreciated, movement of the leg to a position of extension would not be possible when the femoral distractor of the embodiment shown in FIGS. 18-20 has its insertion rod positioned in the medullary canal as shown in FIGS. 5 and 6. However, with the femoral distractor of the embodiments shown in FIGS. 23-33, it is possible to leave the insertion rod 161 in the medullary canal and, following removal of the detachable handle assembly 163, to move the leg from a position of flexion to a position of extension as shown in FIGS. 32 and 33.

Figure 32:
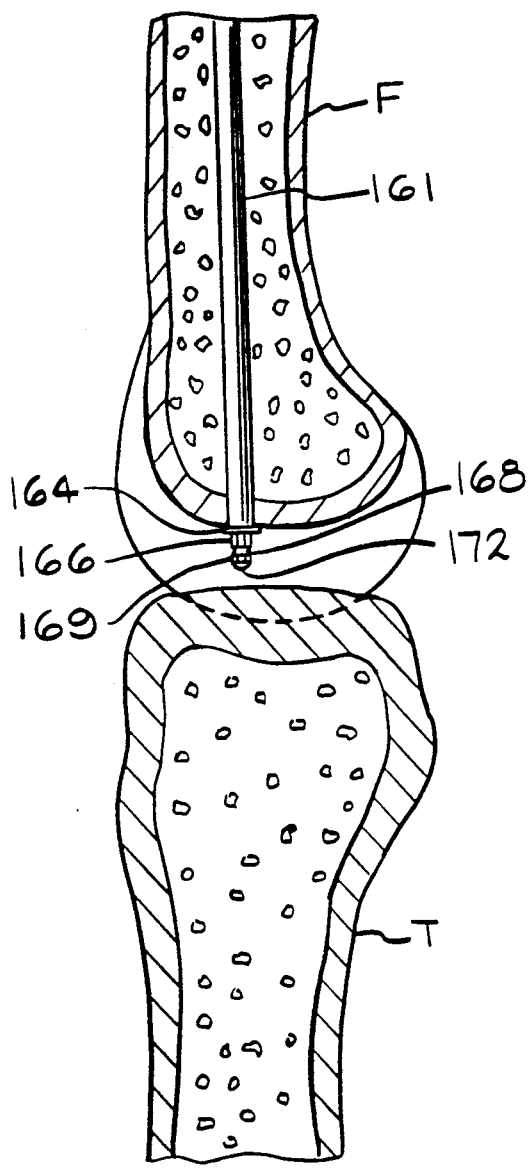
FIGS. 32 and 33 are sectional views showing the insertion rod in the femur with the detachable handle removed and the leg of the patient in extension.

FIG. 32 shows the relative positions of the femur F and tibia T prior to performing osteotomy and with the knee in extension following insertion of the insertion rod 161 in the medullary canal of the femur and removal of the handle assembly therefrom. As can be seen, the flange 164, first section 166, second section 168 and third section 169 project a sufficiently short distance to permit extension of the knee without interference from or damage to the knee. It is also possible to leave the insertion rod 161 in the medullary canal while performing the condylar osteotomies including the distal femoral 2, interior 3, posterior 4 and chamfer 5 cuts.

Figure 33:
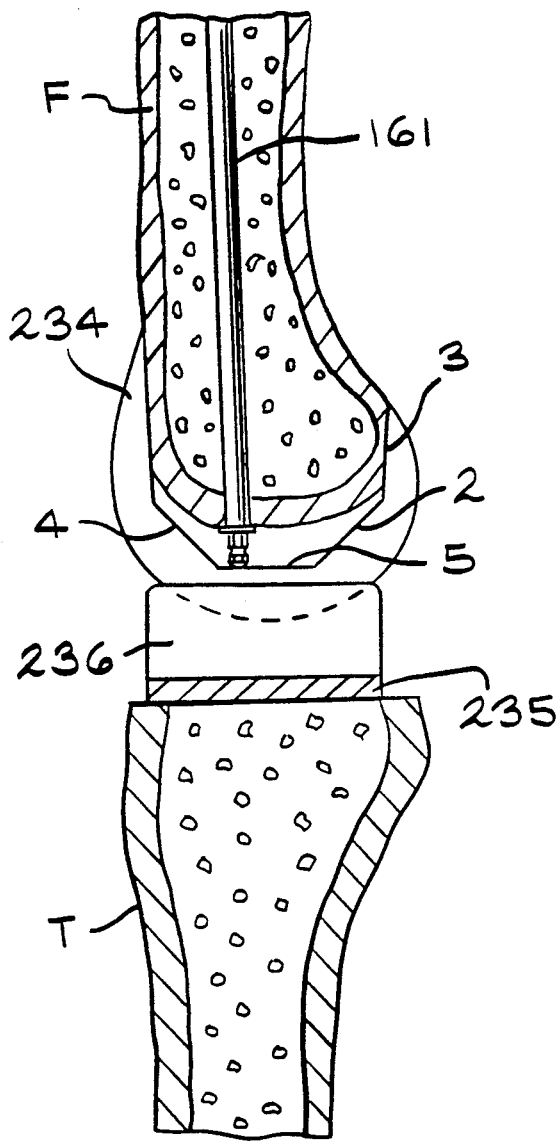

As shown in FIG. 33, a femoral trial 234 has been positioned on the femur F in engagement with the femoral 2, interior 3, posterior 4 and chamfer 5 cuts. Similarly, with respect to the tibia, following osteotomy performed thereon, a tibial base trial 235 and a tibial insert trial 236 are positioned in place on the tibia. By virtue of being able to leave the insertion rod 161 in the medullary canal, it is possible to repeatedly move the knee between positions of flexion and extension while the various thicknesses of tibial insert trials 236 are being tried in order to determine the one most suitable for the specific circumstances.

Other modifications will become readily apparent to those skilled in the art.

I claim:

1. A femoral distractor for use in performing knee surgery comprising a rod and a handle assembly, said rod having first and second sections lying on a longitudinal axis, said first section having a cross-sectional size permitting its insertion in the medullary canal of a human femur, said second section extending to a free end and having engagement means, said handle assembly including (a) coupling means releasably engageable with said engagement means, (b) a support member engaged to said coupling means and being disposed at substantially right angles to said rod and (c) gripping means substantially parallel to said rod spaced from said longitudinal axis and extending along a path generally reverse of the path of 2. A femoral distractor for use in performing knee surgery comprising a rod and a handle assembly, said rod having first and second sections lying on a longitudinal axis, said first section having a cross-sectional size permitting its insertion in the medullary canal of a human femur, said second section extending to a free end and having engagement means, said handle assembly including coupling means releasably engageable with said engagement means, a support member engaged to said coupling means having a segment disposed at an angle to said longitudinal axis, said support member including gripping means spaced from said longitudinal axis and extending along a path generally reverse of the path of said rod but spaced therefrom, said first section having a circular cross-sectional configuration with a chordal section removed to provide planar surface facing said gripping means.

3. The femoral distractor according to claim 2, wherein said first section has a longitudinal groove extending from said end toward said second section.

4. A femoral distractor for use in performing knee surgery comprising a rod and a handle assembly, said rod having first and second sections lying on a longitudinal axis, said first section having a cross-sectional size permitting its insertion in the medullary canal of a human femur, said second section extending to a free end and having engagement means, said handle assembly including coupling means releasably engageable with said engagement means, a support member engaged to said coupling means and having a segment disposed at an angle to said longitudinal axis, said support member including gripping means spaced from said longitudinal axis and extending along a path generally reverse of the path of said rod but spaced therefrom, said engagement means including an annular groove and an enlargement between said groove and said free end and said coupling means comprises a tubular wall having an open end sized to receive at least that portion of said second section including said enlargement and said annular groove, at least one opening in said tubular wall aligned with said annular groove when said second section portion is positioned in said open end, a detent radially displaceable in said opening from an inner position engaging said groove to an outer position spaced from said groove and means retaining said detent in said inner position and releasing said detent for movement to said outer position.

5. The femoral distractor according to claim 4, wherein said means for retaining and releasing said detent includes a sleeve member having a first inner portion engaged with said tubular wall and an enlarged inner portion spaced from said tubular wall, said sleeve being axially displaceable between an engaged position in which said first inner portion is aligned with and engaged by said detent and a disengaged position in which said enlarged inner portion is aligned with said detent and means yieldingly urging said sleeve to said engaged position.

6. The femoral distractor according to claim 4, wherein said tubular wall has an interior surface extending to said open end and defining a chamber having a non-circular cross-sectional configuration and wherein said enlargement has a cross-sectional configuration preventing rotation of said rod relative to said handle assembly when said enlargement is engaged in said chamber.

7. A femoral distractor for use in performing knee surgery comprising a rod and a handle assembly, said rod having first and second sections lying on a longitudinal axis, said first section having a cross-sectional size permitting its insertion in the medullary canal of a human femur, said section extending to a free end and having engagement means, said handle assembly including coupling means releasably engageable with said engagement means, a support member engaged to said coupling means having a segment disposed at an angle to said longitudinal axis, said support member including gripping means spaced from said longitudinal axis and extending along a path generally reverse of the path of said rod but spaced therefrom, said second section having an end portion adjacent said free end, a remote portion spaced from said end portion and an annular groove between said end portion and said remote portion, at least one of said end portion and said remote portion having a non-circular cross-sectional configuration and wherein said handle assembly includes a tubular wall having an interior surface extending to an open end and defining a chamber having a non-circular cross-sectional configuration preventing rotation of said rod relative to said handle assembly when said second section is engaged in said chamber.

8. A femoral distractor for use in performing knee surgery comprising a rod and a handle assembly, said rod having first and second sections lying on a longitudinal axis, said first section having a cross-sectional size permitting its insertion in the medullary canal of a human femur, said second section extending to a free end and having engagement means, said handle assembly including coupling means releasably engageable with said engagement means, a support member engaged to said coupling means and having a segment disposed at an angle to said longitudinal axis, said support member including gripping means spaced from said longitudinal axis and extending along a path generally reverse of the path of said rod but spaced therefrom, said engagement means comprising a stub shaft extending to said free end and bayonet means extending radially outwardly from said stub shaft and said coupling means comprising a housing rotatable relative to said stub shaft and having a chamber with an open end for receiving said second section, said housing having internally disposed slot means for receiving said bayonet means, said slot means extending parallel to said longitudinal axis from said open end and extending perpendicular to said longitudinal axis in an area spaced from said open end.

* * * * *

UNITED STATES PATENT AND TRADEMARK OFFICE
CERTIFICATE OF CORRECTION

PATENT NO. : 5,308,350
DATED : May 3, 1994
INVENTOR(S) : W. E. Michael Mikhail

It is certified that error appears in the above—identified patent and that said Letters Patent is hereby corrected as shown below:

Column 14, line 14,

Last sentence of claim 1 is incomplete, should read after the word "of" insert --said rod--.

Signed and Sealed this

Sixth Day of September, 1994

Attest:

BRUCE LEHMAN

*Attesting Officer*     *Commissioner of Patents and Trademarks*